US008658093B2

(12) United States Patent
Lau et al.

(10) Patent No.: US 8,658,093 B2
(45) Date of Patent: Feb. 25, 2014

(54) DEVICES AND METHODS FOR THE DETECTION OF ANALYTES

(75) Inventors: Aldrich N. K. Lau, Palo Alto, CA (US); Robert G. Eason, Los Gatos, CA (US); Kristian M. Scaboo, Castro Valley, CA (US); Handong Li, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1087 days.

(21) Appl. No.: 12/167,292

(22) Filed: Jul. 3, 2008

(65) Prior Publication Data

US 2009/0142772 A1 Jun. 4, 2009

Related U.S. Application Data

(60) Provisional application No. 60/929,681, filed on Jul. 6, 2007.

(51) Int. Cl.
*G01N 1/26* (2006.01)

(52) U.S. Cl.
USPC ........................................................ 422/50

(58) Field of Classification Search
USPC ........................................................ 422/50
See application file for complete search history.

(56) References Cited

U.S. PATENT DOCUMENTS

| 5,045,172 A | 9/1991 | Guzman |
| 5,202,010 A | 4/1993 | Guzman |
| 5,413,686 A | 5/1995 | Klein et al. |
| 5,741,639 A | 4/1998 | Ensing et al. |
| 5,800,692 A | 9/1998 | Naylor et al. |
| 7,153,407 B2 | 12/2006 | Guzman |
| 2002/0076825 A1* | 6/2002 | Cheng et al. ................... 436/174 |
| 2004/0152097 A1 | 8/2004 | Takenaka |
| 2004/0186359 A1* | 9/2004 | Beaudoin et al. ............. 600/310 |
| 2005/0221337 A1 | 10/2005 | Seeberger et al. |
| 2007/0202535 A1* | 8/2007 | Hirabayashi et al. .......... 435/7.1 |

FOREIGN PATENT DOCUMENTS

WO 2005/064333 7/2005

OTHER PUBLICATIONS

Disney, et al., Chemistry and Biology, vol. 11, 1701, Dec. 2004.
Timmer, et al., Current Opinion in Chemical Biology, 11, 59-65, 2007.
Bertozzi, et al., Science 2001, 291, 2357-2364.
Rojo, et al., Topics Curr. Chern., 218, 45-92, 2002.
Santacroce, Polym. Preprints, 46, 1114, 2005.
Tarasenko, et al., Carohydrate Res., 339, 2859-2870, 2004.
Galanina, et al., Spectrochim. Acta, Part A, 57, 2285-2296, 2001.
Levon, et al., Macromol. Symp., 201, 114-117, 2003.
Houseman, et al., Langmuir, 19, 1522-1531, 2003.
Sames, et al., Nature 1997, 389, 587.
Sharma, et al., Polym. Prepr.,43 (2), 736-737, 2002.
Ellington, et al., "In Vitro Selection of RNA Molecules that Bind Specific Ligands," Nature, 346(6287):818-22, 1990.

(Continued)

*Primary Examiner* — Mark Shibuya
*Assistant Examiner* — Pensee Do
(74) *Attorney, Agent, or Firm* — Applied Biosystems, LLC

(57) ABSTRACT

System and methods for detecting analytes such as pathogenic cells are described. The methods allow for the direct measurement of analytes such as pathogenic organisms without the need for sample preparation and/or PCR. The devices can be used individually as point-of-use sensors for airborne pathogens and other pathogenic organisms in foods and agriculture products.

14 Claims, 29 Drawing Sheets

(56) References Cited

OTHER PUBLICATIONS

Bock, et al., "Selection Of Single-Stranded DNA Molecules That Bind and Inhibit Human Thrombin," Nature, 355 (6360):564-6, 1992.
Hoppe-Seyler, et al., "Peptide Aptamers: Powerful New Tools for Molecular Medicine," J. Mol. Med., 78(8):426-30, 2000.
Carothers, et al., "Informational Complexity and Functional Activity Of RNA Structures," J. Am. Chem. Soc., 126 (16):5130-7, 2004.
Cohen, et al., "An Artificial Cell-Cycle Inhibitor Isolated From A Combinatorial Library," PNAS 95(24):14272-7, 1998.
Binkowski, et al., "Ligand Regulated Peptides: A General Approach For Selection Of Ligand Regulated Peptide-Protein Interactions," Chem. & Biol., 12 (7):847-55, 2005.
Sullenger, et al., "Emerging Clinical Applications Of RNA," Nature 2002, 418:252-258.
Ng, et al., "Pegaptanib, A Targeted Anti-VEGF Aptamer For Ocular Vascular Disease," Nat. Rev. Drug Discov., 5:123-132, 2006.
Bakalova, et al., Anal. Chem., ASAP Article 10.1021, Jul. 14, 2006.
Thies, et al., Polym. Prepr., 46, 1235-1236, 2005.
Park, et al., J. Am. Chem. Soc., 126, 4812-4819, 2004.
Wang, "Carbohydrate Microarrays," Proteomics, 3, 2167-2175, 2003.
Houseman, et al., "Carbohydrate Arrays For The Evaluation Of Protein Binding And Enzymatic Modification," Chem. Biol., 9, 443-454, 2002b.
Fritz, J. Am. Chem. Soc., 122(49), 12411-12412, 2000.
Kaye, et al., Anal. Chem., 68(9), 1658-1660, 1996.
Yin, et al., Anal. Chem., 77(2), 527-533, 2005.
Mammen, et al., Agnew. Chem. Int. Ed., 37, 2754-2794, 1998.
Lis, et al., Chem. Rev., 98, 637-674, 1998.
Housemsn, et al., Nature Technology, 20, 270-274, 2002.
Wang, et al., Nature Technology, 20, 275-281, 2002.
Rider, et al., Science 2003, 301, 213-215.
Love, et al., "Carbohydrate Arrays as Tools for Glycomics," Angewandte Chemie. International Edition, vol. 41, No. 19, Oct. 2002, 3583-3586.
Smith, et al., "Surface Plasmon Resonance Imaging Studies of Protein-Carbohydrate Interactions," Journal of the American Chemical Society, vol. 125, No. 20, May 2003, 6140-6148.
Ngundi, et al., "Detection of Bacterial Toxins with Monosaccharide Arrays," Biosensor & Bioelectronic, vol. 21, No. 7, Jan. 2006, 1195-1201.
PCT/US08/069126, International Preliminary Report on Patentability mailed Jan. 21, 2010.

* cited by examiner

FITC-lectin
LENS
CULINARIS
(LENTIL)

a-Man
a-Fuc
β-Glc
β-Gal
a-GlcNAc
β-GlcNAc
a-Neu5Ac

NOT TREATED | PEG24 TREATED

PEG24 TREATED     NOT TREATED

SPOTTING PATTERN:

MANOSE
GLUCOSE
GALACTOSE
MALTOSE
FUCOSE
GlcNAc
GalNAc
NeuNAc

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: A polypeptide moiety that is linked to a
      recurring unit to form an immobilized macromolecule in the claimed
      apparatus.

<400> SEQUENCE: 2

Cys Gly Gly Gly Val Lys Pro Leu Phe His Asn
1               5                   10

<210> SEQ ID NO 2
<211> LENGTH: 4
<212> TYPE: PRT
<213> ORGANISM: Artificial Sequence
<220> FEATURE:
<223> OTHER INFORMATION: The reducing active site of bacterial protein
      Thioredoxin-A into which a variable loop can be inserted.

<400> SEQUENCE: 2

Cys Gly Pro Cys
1
```

DEVICES AND METHODS FOR THE DETECTION OF ANALYTES This application claims the benefit of Provisional U.S. Patent Application Ser. No. 60/929,681, filed on Jul. 6, 2007, which is incorporated by reference herein in its entirety.

Pursuant to the provisions of 37 C.F.R. §1.52(e)(5), the sequence listing text file named 67143_Seq_Listing.txt, created on Jul. 2, 2008 and having a size of 555 bytes, and which is being submitted herewith, is incorporated by reference herein in its entirety.

The section headings used herein are for organizational purposes only and should not be construed as limiting the subject matter described herein in any way.

FIELD

This application relates generally to systems and methods for detecting biological target analytes such as pathogenic cells in a sample.

INTRODUCTION

Affinity ligand-binding assays are widely used in biochemical and clinical research. In most common assay methods, binding proceeds until an equilibrium condition has been obtained which can result in relatively long incubation times. In addition, the target analyte is typically present in relatively low concentrations in a complex sample mixture. Under these conditions, the target analyte may never encounter sufficient binding ligands to be detectable. The analysis of target molecules in complex mixtures therefore often requires pretreatment steps. For example, if the analyte is present in low concentrations, it may first need to be concentrated in order to be detected by standard analytical techniques. Second, if it is present in a complex mixture of similar compounds, a cleanup or purification step may be required to remove certain components of the mixture to allow for detection of the target analyte.

It is, therefore, desirable to have a simple device which can enrich analytes to have higher effective concentration thereby achieving rapid target analyte/ligand binding and detection even when the target analyte is present at relatively low concentrations in complex sample mixtures.

SUMMARY

An apparatus is provided which comprises:
a support having a surface comprising a plurality of discrete analyte binding areas arranged in a spaced relationship, wherein each of the discrete analyte binding areas comprises an immobilized polymer which comprises a plurality of ligands which specifically bind to a target analyte and;
a cover spaced from the surface of the support and forming a flow channel therebetween, the cover having a first surface facing toward the support and a second surface facing away from the support.

A method of detecting the presence, amount and/or location of a target analyte in a liquid sample is also provided which comprises:
introducing the liquid sample into the flow channel of an apparatus as set forth above, wherein at least one of the discrete analyte binding areas comprises an immobilized polymer which comprises at least one ligand which specifically binds to the target analyte;
flowing the liquid sample across the surface of the support such that the sample contacts each of the discrete analyte binding areas;
allowing target analyte in the sample to bind to the immobilized ligand;
washing the surface of the support;
introducing a composition comprising a reporter reagent into the flow channel of the apparatus, wherein the reporter reagent comprises a detectable moiety and a ligand which specifically binds to the target analyte when the target analyte is bound to the immobilized ligand;
flowing the composition comprising the reporter reagent across the upper surface of the support such that the composition comprising the reporter reagent contacts each of the discrete analyte binding areas;
washing the surface of the support;
detecting reporter reagent on the surface of the support.

By detecting "on the surface" it is meant that detection occurs in close proximity (i.e., on or near) the surface.

A method of detecting the presence, amount and/or location of a target analyte in a liquid sample is also provided which comprises:
combining the liquid sample with one or more magnetic beads, wherein an outer surface of each of the magnetic beads comprises an immobilized polymer which comprises a plurality of ligands which specifically bind to a target analyte;
introducing the liquid sample and magnetic beads into a flow channel of an apparatus comprising a cover which is spaced from a support layer;
applying a magnetic field to the liquid in the flow channel through the support layer to immobilize the magnetic beads on the support layer;
washing the support layer while applying the magnetic field;
introducing a composition comprising a reporter reagent into the flow channel, wherein the reporter reagent comprises a detectable moiety and a ligand which specifically binds to the target analyte when the target analyte is bound to the immobilized ligand on the magnetic bead;
allowing the reporter reagent to bind to the target analyte;
washing the support layer while applying the magnetic field; and
detecting reporter reagent in the flow channel.

An apparatus is also provided which comprises:
a first reservoir;
a second reservoir;
a plurality of flow channels each having an internal surface, a first end in fluid communication with the first reservoir and a second end in fluid communication with the second reservoir;
wherein the internal surface of each of the flow channels comprises a plurality of discrete analyte binding areas spaced along the length of the flow channel, wherein each of the discrete analyte binding areas comprises an immobilized ligand which specifically binds to a target analyte and;
wherein a fluid flowing from the first reservoir to the second reservoir through the flow channels contacts the discrete analyte binding areas on the internal surfaces of the flow channels.

A method of detecting the presence and/or amount of an analyte in a liquid sample is also provided which comprises:
placing the liquid sample in the first reservoir of an apparatus as set forth above;

combining the liquid sample with a reporter reagent;
flowing the liquid sample through the plurality of flow channels in the direction of the second reservoir;
washing the internal surfaces of the flow channels;
detecting reporter reagent on the internal surfaces of the plurality of flow channels;
wherein at least one of the immobilized ligands specifically binds to the analyte and wherein the reporter reagent comprises a detectable moiety and a ligand which specifically binds to the analyte and which does not interfere with the binding of the analyte to the immobilized ligand.

A method of detecting the presence and/or amount of an analyte in a liquid sample is also provided which comprises:
placing the liquid sample in the first reservoir of an apparatus as set forth above;
flowing the liquid sample through the plurality of flow channels in the direction of the second reservoir;
optionally, washing the internal surfaces of the flow channels
subsequently flowing a reporter reagent through the plurality of flow channels in the direction of the second reservoir;
washing the internal surfaces of the flow channels;
detecting reporter reagent on the internal surfaces of the plurality of flow channels;
wherein at least one of the immobilized ligands specifically binds to the analyte and wherein the reporter reagent comprises a detectable moiety and a ligand which specifically binds to the analyte when the analyte is bound to the immobilized ligand.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF THE VARIOUS EMBODIMENTS

Figure 1A:
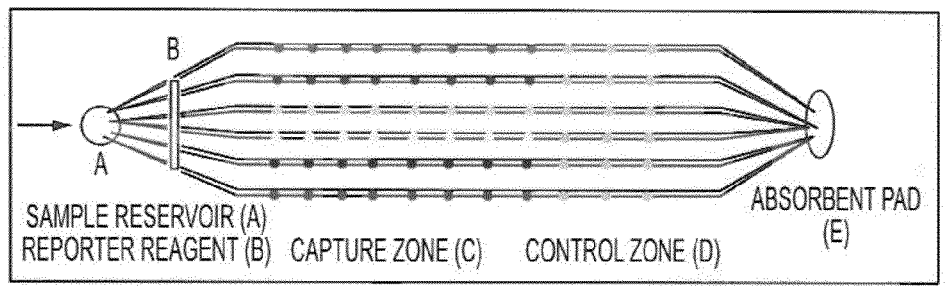
FIG. 1A is a schematic of a device for detecting analyte in a sample.

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." It should also be understood that in some embodiments the order of steps or order for performing certain actions is immaterial so long as the present teachings remain operable. Moreover, in some embodiments two or more steps or actions can be conducted simultaneously.

As used herein, the term "ligand" refers to any molecule that binds to another molecule. Ligands include biological molecules such as aptamers, proteins, polypeptides, carbohydrates, lectins, saccharides, glycoproteins and glycopeptides. Ligands can bind to other biological molecules including, but not limited to, proteins, glycoproteins, glycolipids, glycosaminoglycans and proteoglycans. Ligands as used herein includes both mono-valent ligands (a molecule with a single ligand moiety) and polyvalent ligands (a molecule with 2 or more ligand moieties). For example, the ligand can be a macromolecule which comprises a plurality of ligand moieties.

As used herein, the term "saccharide" refers to any molecule comprising a saccharide moiety. The term "saccharide" therefore encompasses both monosaccharides and polysaccarides including oligosaccharides, disaccharides, tri-saccharides, tetra-saccharides, etc. "Saccharide" may also be used to refer to biomolecules containing saccharides and other moieties. Examples include, but are not limited to: sialic acid; amine-containing saccharides and N-acylated derivatives thereof; saccharide conjugates of cyclitols and other glycans; and saccharide conjugates of aminocyclitols (e.g., aminoglycosides) and N-modified derivatives thereof.

As used herein, the term "glycoconjugate" refers to a carbohydrate (e.g., a saccharide) covalently linked to another chemical group. The chemical group can be, for example, a polymer. Non-polymeric chemical groups can also be used.

As used herein, the phrase "polyvalent glycoconjugate" refers to glycoconjugates comprising a plurality of carbohydrates covalently linked to another chemical group.

As used herein, the term "polysaccharide" refers to polymers made up of a plurality of monosaccharide units joined together by glycosidic linkages.

As used herein, the term "glycoprotein" refers to a biomolecule comprising a protein and a carbohydrate covalently linked together.

As used herein, the term "oligosaccharide" refers to a polysaccharide containing a small number (e.g., three to ten) saccharide units.

According to some embodiments, an apparatus is provided which comprises: a first reservoir; a second reservoir; a plurality of flow channels each having an internal surface, a first end in fluid communication with the first reservoir and a second end in fluid communication with the second reservoir. The internal surfaces of each of the flow channels comprises a plurality of discrete analyte binding areas spaced along the length of the flow channel. Each of the discrete analyte binding areas comprises an immobilized ligand (e.g., a polyvalent glycoconjugate) which specifically binds to a target analyte. A fluid flowing from the first reservoir to the second reservoir through the flow channels contacts the discrete analyte binding areas on the internal surfaces of the flow channels. According to some embodiments, the device can further comprise a third reservoir in fluid communication with the flow channels at a point along the length of the flow channels between the first reservoir and the discrete analyte binding region nearest the first reservoir. This third reservoir can contain a reporter reagent. An exemplary device of this type is illustrated in FIG. 1A. Although the third reservoir is depicted in FIG. 1A as being a single reservoir, the third reservoir may also comprise a plurality of reservoirs. For example, a separate reservoir can be used to supply each of the flow channels.

A method of detecting the presence, amount and/or location of an analyte in a liquid sample using an apparatus as set forth above is also provided. The method comprises: placing the liquid sample in the first reservoir of the apparatus; combining the liquid sample with a reporter reagent; flowing the liquid sample through the plurality of flow channels in the direction of the second reservoir; detecting reporter reagent on the internal surfaces of the plurality of flow channels; wherein at least one of the immobilized ligands specifically binds to the analyte and wherein the reporter reagent comprises a detectable moiety and a ligand which specifically binds to the analyte and which does not interfere with the binding of the analyte to the immobilized ligand. The liquid sample can be combined with the reporter reagent and the sample in the first reservoir. Alternatively, the apparatus can further comprise a third reservoir in fluid communication with the plurality of flow channels at a point along the length of the flow channels between the first reservoir and the discrete area closest to the first reservoir as shown in FIG. 1A. The composition comprising the reporter reagent can be added to the third reservoir such that the sample contacts the reporter reagent and is combined therewith while flowing through the plurality of flow channels.

When a sample (e.g., urine, saliva, whole blood/serum, or an environmental sample) is introduced into the sample reservoir (A) of the device shown in FIG. 1A, capillary effects can be used to propel the sample liquids through the flow channels. The sample may include an appropriate buffer. The flow channels can be capillary microchannels or wicks. Capillary forces provide certain advantages. In particular, they are self-contained, scalable, free of dead volume, and pre-programmable.

As set forth above, the reporter reagent can be loaded into a first reservoir in the front end of each flow channel (e.g., capillary channel or wick). As shown in FIG. 1A, the sample moving along the flow channel can contact and combine with reporter reagent (B) in a second reservoir. The reporter reagent (B) in the second reservoir can then migrate with the analyte to the affinity ligand array capture zone containing immobilized ligands. In this zone, the analyte-reporter conjugate complex can bind to the immobilized ligand. Unreacted reporter agent, along with unreacted analyte, can then continue to flow to the end of the flow channels and into an absorbent material (E). The absorbent material, which is optional, can be used to aid in drawing sample through the flow channels of the device.

As also shown in FIG. 1A, a control array zone (D) containing a universal ligand can be placed next to capture zone. The universal ligand is a ligand that binds the reporter reagent regardless of whether the target analyte is present. The control array zone can be used for calibration and validation purpose. In addition, the array can be scanned in a time-resolved mode to provide binding kinetics, quantitation and maximum sensitivity.

Although a second reservoir is shown in FIG. 1A, the second reservoir is optional. Moreover, although shown in two zones in FIG. 1A, the reporter reagent (B) and the sample reservoir (A) can also be integrated into one zone. In particular, the reporter reagent can also be combined with the sample in the first reservoir.

A variety of platforms of affinity ligand arrays can be designed in the capture zone. For example, plural sets (or rows) of affinity ligands can be used to detect multiple target analytes in one sample (A). An array of the same ligand in the same row can be used to measure binding kinetics and to generate a titration curve.

Figure 1B:
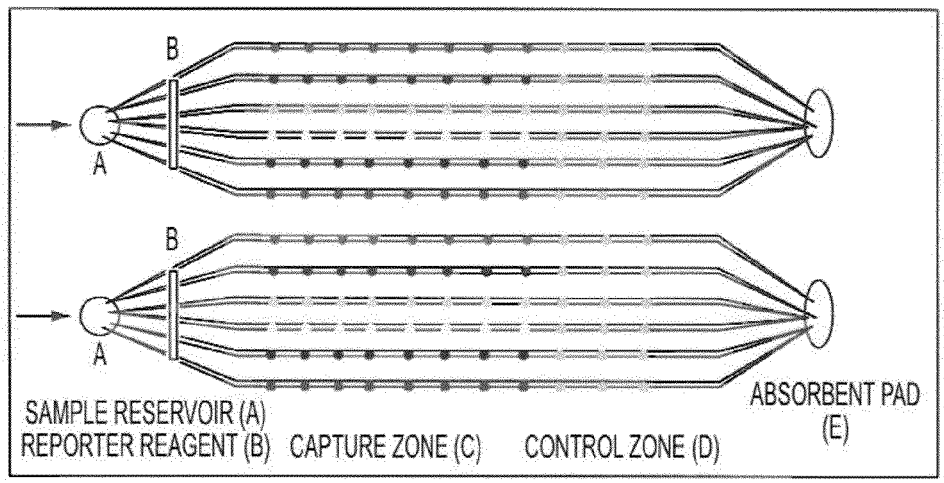
FIG. 1B is a schematic of a device for detecting analyte in multiple samples.

As shown in FIG. 1B, multiple samples can be processed on a single device. FIG. 1B is a schematic of an array-in-an array microfluidic chip which allows multiple samples to be processed on a single device. Although a device is shown in FIG. 1B which allows two samples to be processed, devices which allow for the processing of three or more samples can also be used. Multilayers of arrays on different planes (i.e., levels) on top on one another can also be employed. In this manner, side-by-side comparisons of two or more different samples can be conducted using a single device.

Figure 2:
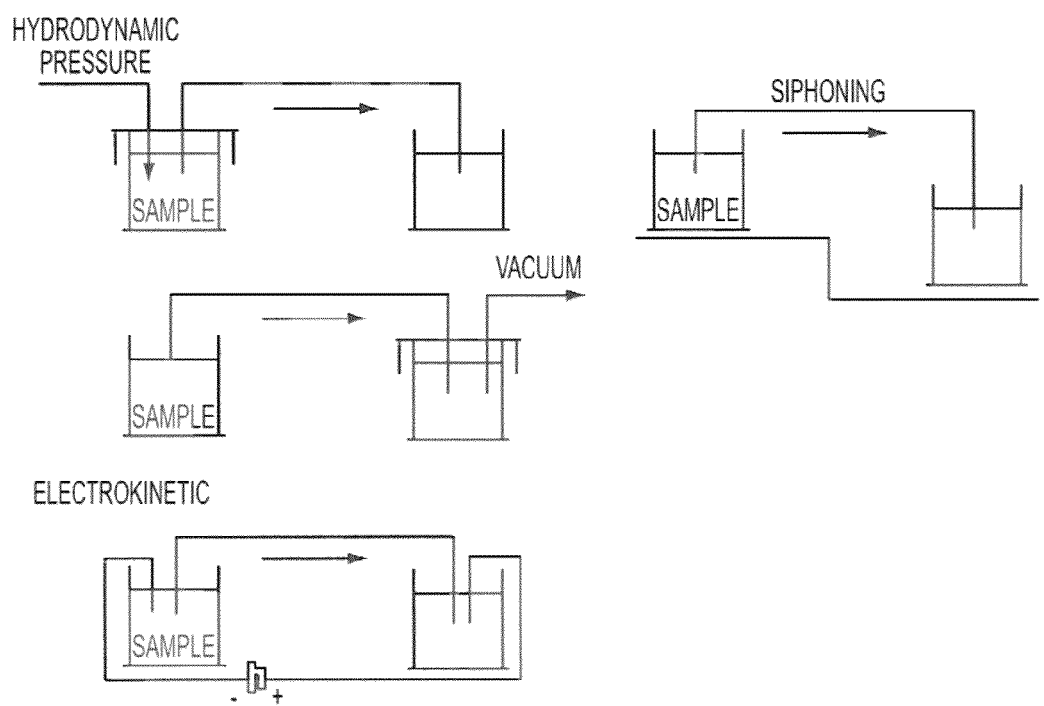
FIG. 2 is a schematic illustrating various different mechanisms which can be used to drive sample fluidics in the device of FIGS. 1A and 1B.

The sample can also be driven through the flow channels of the device by forces other than capillary or wicking effects. FIG. 2 illustrates various mechanisms which can be used to drive samples through the binding zones. The mechanisms depicted in FIG. 2 include pressure, vacuum, siphoning, and the application of an electrical field. These mechanisms are merely exemplary and other mechanisms can also be used to drive samples through the flow channels.

An apparatus is also provided which comprises: a support having a surface comprising plurality of discrete analyte binding areas arranged in a spaced relationship; and a cover spaced from the surface of the support and forming a flow channel therebetween. Each of the discrete analyte binding areas comprises an immobilized polymer which comprises a plurality of ligands which specifically bind to a target analyte. The cover has a first surface facing toward the support and a second surface facing away from the support. According to some embodiments of the invention, the device comprises: a planar cover, a planar substrate onto which an array of ligands is immobilized, each of which is specific to a target pathogenic cell, and a space or gap between the cover and the substrate to accommodate an aqueous analyte.

Figure 3:
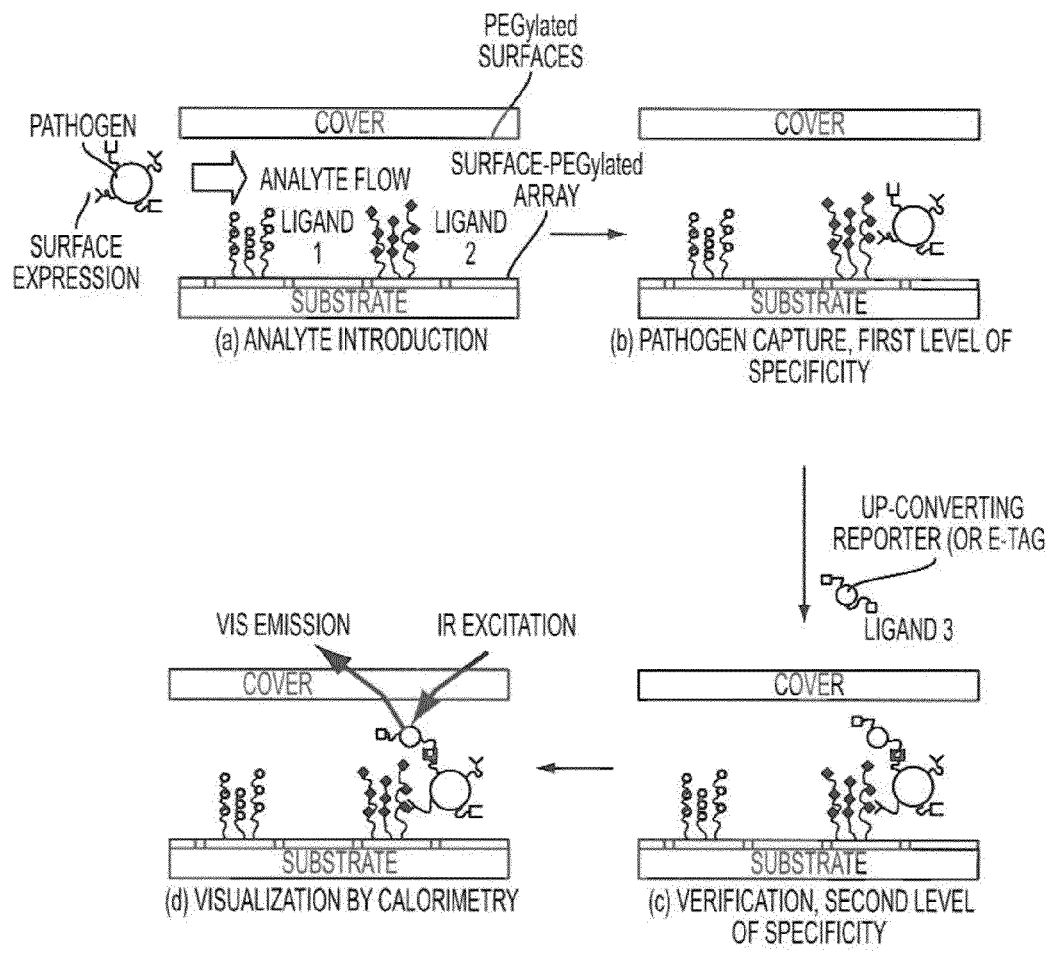
FIG. 3 is a schematic illustrating the detection of pathogens based on immobilized ligands in a sandwich-type assay device.

An exemplary schematic of a device of this type is illustrated in FIG. 3. The device can be used in an assay for pathogenic cells. In particular, when an aqueous analyte containing a plurality of pathogenic cells is introduced into the device as shown in step (a) of FIG. 3, one of the ligands can bind to the carbohydrates, proteins, peptides, or glycoconjugates expressed on the surface of a target pathogenic cell, capturing it onto the array surface as illustrated in step (b) of FIG. 3. The substrate surface can then be rinsed to rid of other cells and contaminants. In a subsequent step, a reporter reagent comprising a second ligand that is capable of binding specifically to the captured pathogen cell can be introduced into the device as shown in step (c) of FIG. 3. The use of a second ligand capable of binding specifically to the captured pathogen cell can improve the specificity for detection of the device. The captured cell/reporter reagent complex can then be detected as shown in step (d) of FIG. 3. For example, the reporter reagent can comprise an up-converting phosphor and the captured cell/reporter reagent complex can be detected by irradiation with infrared (IR) light and detection of the visible emission (VIS emission) from the phosphor as shown in step (d) of FIG. 3.

Figure 4:
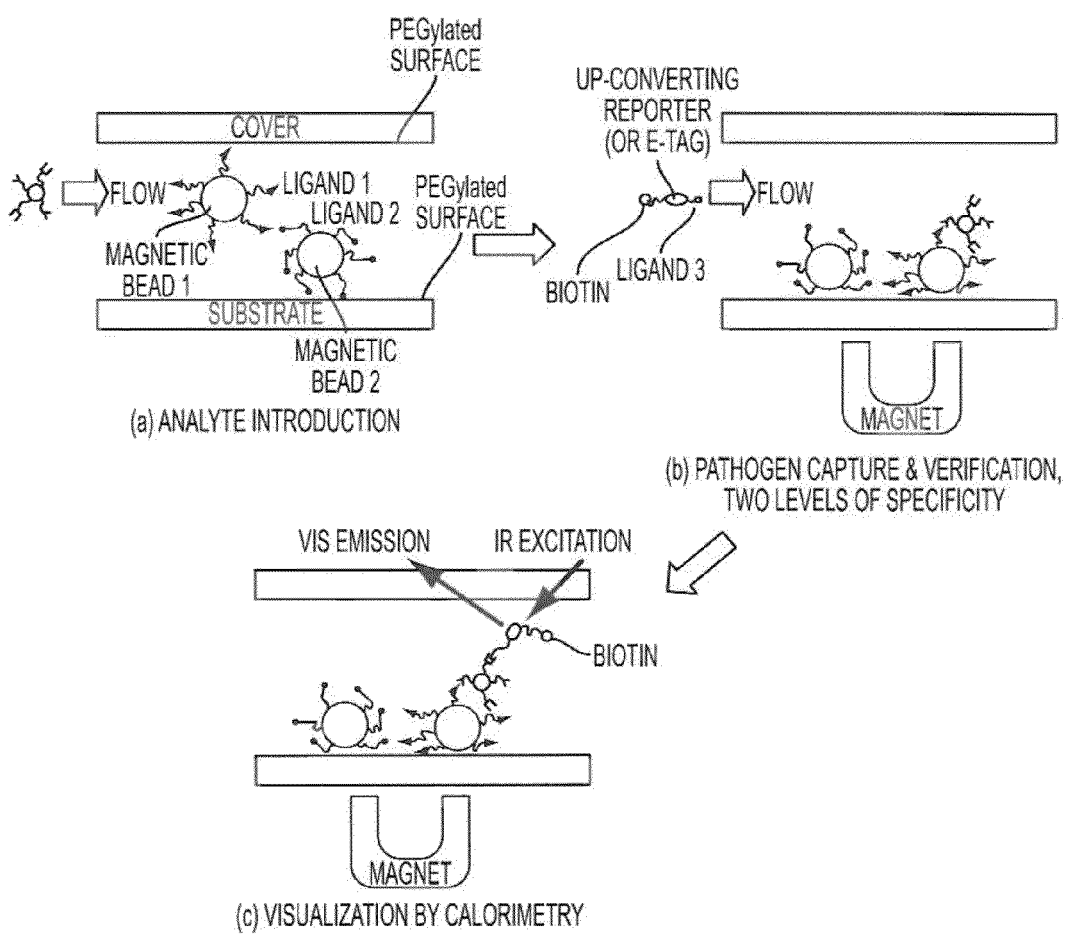
FIG. 4 is a schematic illustrating the detection of pathogens based on immobilized ligands on the surface of magnetic beads.

According to some embodiments of the invention, the first ligand can be immobilized on the outer surface of a magnetic bead as shown in FIG. 4. As shown in step (a) of FIG. 4, the magnetic beads having immobilized ligand thereon can be positioned in the space between a planar cover and a planar substrate of a device. An aqueous sample containing a plurality of pathogenic cells can then be introduced into the space containing the magnetic beads as also shown in step (a) of FIG. 4. All of the magnetic beads, including those with and without the captured target pathogen cells, can then be pulled down with a magnet onto the surface of the substrate as shown in step (b) of FIG. 4. The surface of the substrate can then be rinsed to remove other cells and contaminants. A reporter having a second ligand specific to the target pathogenic cell can then be introduced as shown in step (c) of FIG. 4. The space between the cover and the substrate and their surfaces can then be rinsed to rid of excess reporter reagent and contaminants. The captured cell/reporter reagent complex can then be detected as shown in step (c) of FIG. 4. For example, the reporter reagent can comprise an up-converting phosphor and the captured cell/reporter reagent complex can be detected by irradiation with infrared (IR) light and detection of the visible emission (VIS emission) from the phosphor as shown in step (c) of FIG. 4.

As set forth in more detail below, the reporter reagent can comprise an up-converting reporter which emits light in the visible spectrum when exposed to infrared (IR) irradiation. Compared with a negative control, visible light emission upon IR radiation can be used to indicate the presence of target pathogens. Although up-coverting reporters are illustrated in FIGS. 3 and 4, other types of reporters can also be used. In various embodiments of the invention, the reporter reagent can comprise a dye molecule, a quantum dot, or an electrochemically active molecule (i.e., an E-tag). According to some embodiments, the reporter reagent comprises an E-tag for electrochemical detection of a pathogen. The discrete areas on the surface of the substrate can be indium tin oxide (ITO) or gold having polyvalent glycoconjugates immobilized thereon for pathogen binding. The conductive discrete areas can be addressed individually be an electronic device. A non-limiting example of such a device is a random access device. For electrochemical detection, the cover can comprise ITO or a transparent gold surface facing toward the substrate. Examples of methods of electrochemical detection include, but are not limited to, cyclic voltammetry, differential pulse voltammetry, chronopotentiometry, chronoamperometry and impedance spectroscopy.

Figure 5:
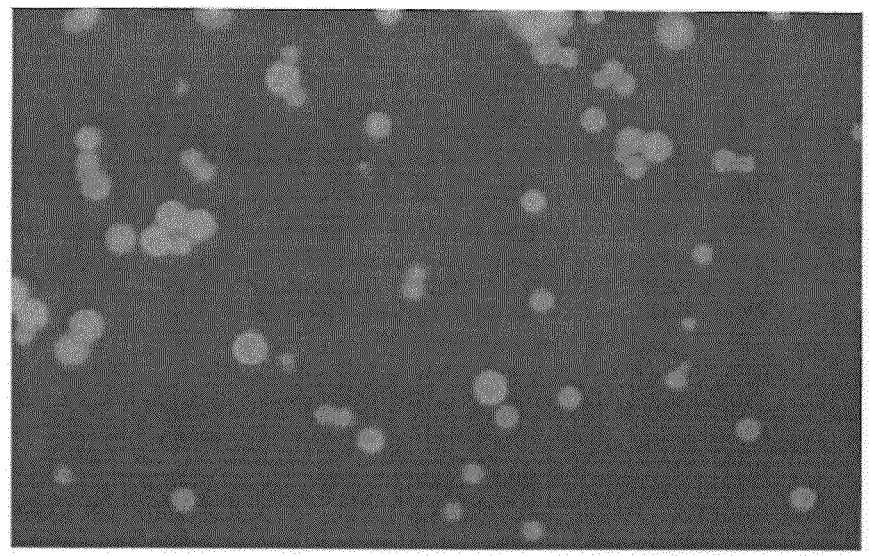
FIG. 5 is a photograph of a precursor for dyed magnetic polystyrene beads with surface carboxylic acid groups at a magnification of 400×.

Any bead or other solid particulate material which can be attracted by a magnetic field can be used. For example, the magnetic beads can be magnetic polystyrene beads which have been dyed. Dyed polystyrene magnetic beads having surface carboxylic groups have been prepared and are shown in FIG. 5 at a magnification of 400×. The surface carboxylic groups on the beads can be used to conjugate ligands and biotin molecules.

Figure 6A:
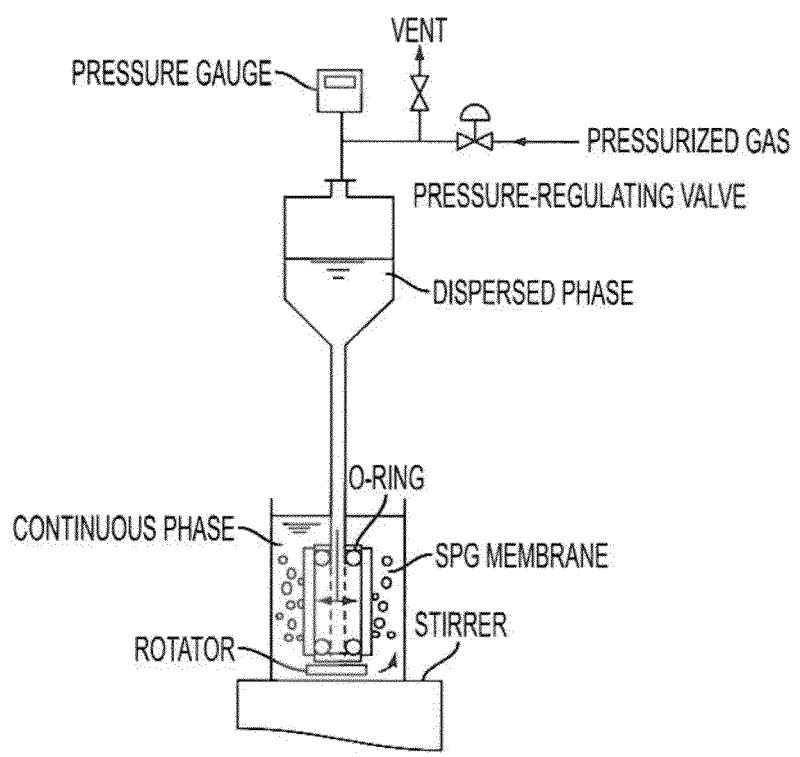
FIG. 6A is a schematic of a membrane emulsion polymerization apparatus.
Figure 6B:
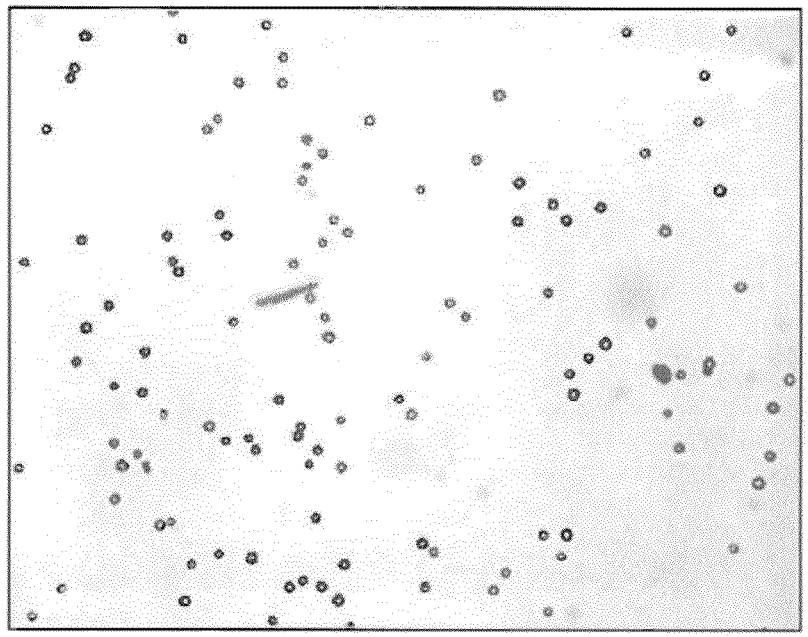
FIG. 6B is a photograph illustrating the distribution of particle sizes for polystyrene microspheres made using the membrane emulsion polymerization apparatus of FIG. 6A.
Figure 6C:
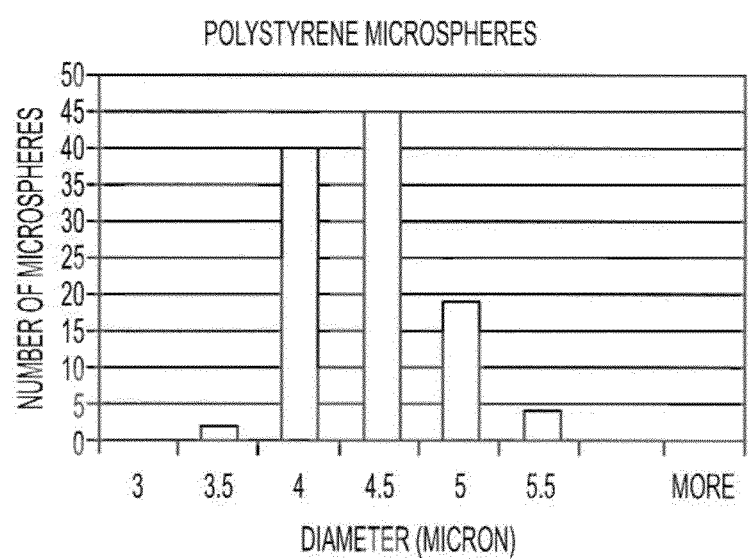
FIG. 6C illustrates a bar graph showing the particle size distribution for polystyrene microspheres made using the membrane emulsion polymerization apparatus of FIG. 6A.

According to some embodiments, the particle size of the magnetic beads can be controlled using membrane emulsion polymerization. Polystyrene beads having a narrow size distribution with a CV less than 10% can be prepared using membrane emulsification as shown in FIGS. 6A-6C wherein FIG. 6A is a schematic of a membrane emulsion polymerization apparatus, FIG. 6B is a photograph illustrating the distribution of particle sizes for polystyrene microspheres made using the membrane emulsion polymerization apparatus of FIG. 6A and FIG. 6C illustrates a bar graph showing the particle size distribution for polystyrene microspheres made using the membrane emulsion polymerization apparatus of FIG. 6A.

In order to reduce and/or eliminate non-specific adsorption of cells and biomolecules such as protein, the surfaces of the cover and the unreactive areas of the substrate or flow channels of the above-described devices can comprise poly(ethylene glycol) moieties (i.e., PEG moieties). For example, these surfaces can be PEGylated or surface modified to contain PEG moieties. The linkages that anchor the ligands onto the array substrates can also comprise poly(ethylene glycol) (PEG) moieties.

Ligands

Non-limiting examples of ligands which can be employed are described below. These ligands include, but are not limited to, proteins, polypeptides, saccharides and their derivatives, nucleic acids (e.g., oligonucleotides or DNA), small molecules and antibodies.

Saccharides

Carbohydrates can be classified into mono-, di-, tri-, oligo-, poly- and hetero-saccharides. The smallest carbohydrates are monosaccharides such as glucose and mannose. Polysaccharides such as starch, cellulose, glycan and fiber can be large and even indeterminate in length. The terms "carbohydrate" and "saccharide" are used interchangeably herein.

Carbohydrates displayed on the surface of cells play critical roles in cell-cell recognition, adhesion, signaling between cells, and as markers for disease progression. Neural cells use carbohydrates to facilitate development and regeneration; cancer cell progression is often characterized by increased carbohydrate-dependent cell adhesion and the enhanced display of carbohydrates on the cell surface; viruses recognize carbohydrates to gain entry into host cells; and bacteria bind to carbohydrates for host cell adhesion. Identification of the specific saccharides involved in these processes is important to better understand cell-cell recognition at the molecular level and to aid the design of therapeutics and diagnostic tools (Disney et al., Chemistry and Biology, vol 11, 1701, December, 2004).

Many interactions at cell-cell interfaces involve multibinding events that occur simultaneously. This "multivalent" type of binding amplifies affinities relative to interactions that involve only a single ligand. Cell-surface carbohydrates are exploited by many pathogens for adherence to tissues and entry into host cells. Microarrays present carbohydrates in an ideal manner to study cell-cell interactions because they can accommodate multivalent binding.

Shown below are examples of monosaccharides which can be used to construct microarrays to study interactions with bacteria.

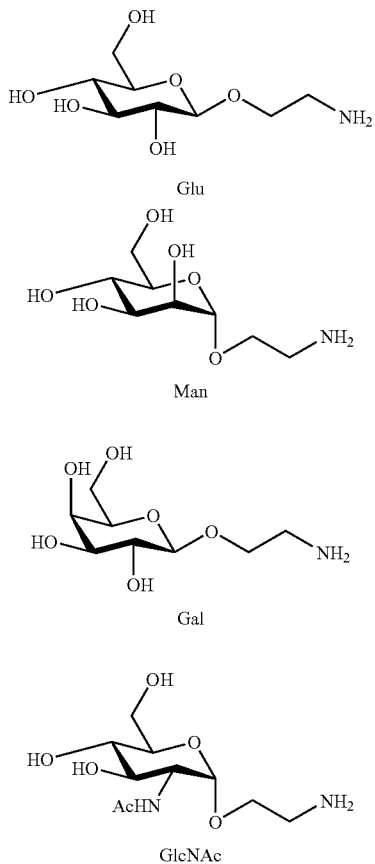

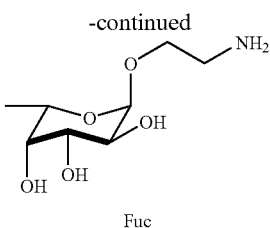

Fuc

Exemplary carbohydrate ligands that can be used and the bacterium to which they bind are set forth in the following table.

| Carbohydrate Ligand | Bacterium |
| --- | --- |
| Mannose | Type 1 fimbriated *E. coli* |
| N-glycolylneuaminic acid | *E. Coli* K99 |
| N-Acetylneuraminic acid | *P. aeruginosa* |
| Galactose | *Bordetella pertussi* |
| Methyl α-mannoside | *Klebsiella pneumoniae* |
| NeuAc(α 2-3)lactose | *Helicobacter pylori* |

Figure 7A:
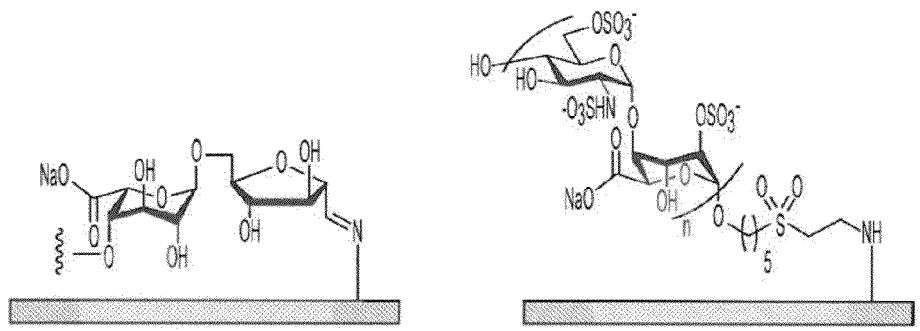
FIG. 7 is a schematic illustrating a heparin microarray which can be used to study interactions with bacteria.
Figure 7B:
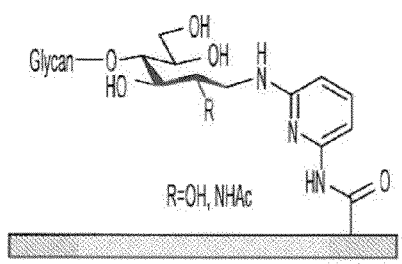

Proteins and cells have much stronger affinity binding to di- or poly-saccharides such as heparins (Timmer et al., Current Opinion in Chemical Biology 2007, 11:1-7). Heparins can therefore also be used to construct microarrays to study interactions with bacteria. A heparin microarray is depicted in FIG. 7.

Carbohydrates

Exogenously supplied monosaccharides can be taken up by cells and converted to monosaccharide building blocks that are subsequently assembled by glycosyltransferases into oligosaccharides bound to a protein. Once expressed on the cell surface, these glycoproteins can serve as ligands for receptor on other cells or pathogens (Bertozzi et al., Science 2001, 291, 2357-2364).

Carbohydrate-carbohydrate interaction (CCI) between glycolipids on opposing cell surfaces mediate cell adhesion in multi-cellular development and cancer metastases (Rojo et al., Topics Curr. Chem. 2002, 218, 45-92). It has been reported that lactosylated surface exhibit strong interaction with melanoma cell with ganglioside sialosyllactosylceramide ($MG_3$) surface expression (Santacroce, Polym. Preprints 2005, 46, 1114).

Figure 8:
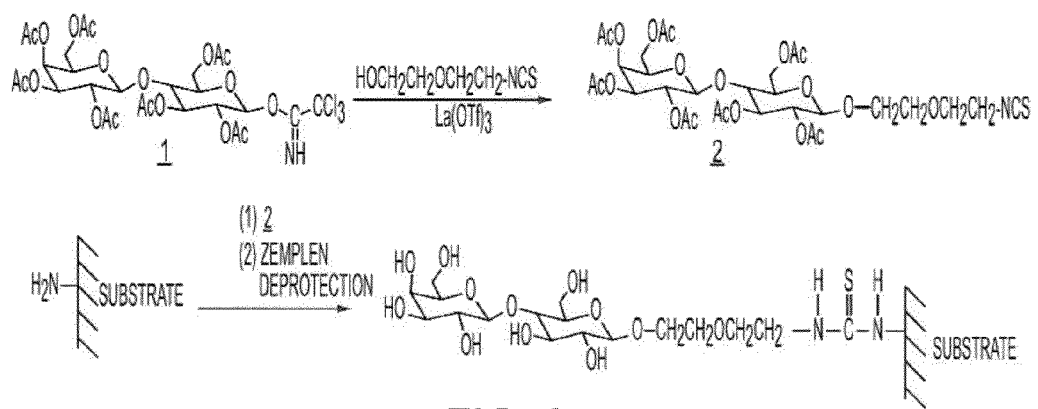
FIG. 8 is a reaction scheme for surface immobilization of a carbohydrate (i.e., lactose) on a surface aminated substrate.

According to some embodiments, surface immobilized carbohydrates such as lactose isothiocyanate 2, prepared by reacting acetylated lactose trichloroacetimidate 1 with diethylene glycol derived isothiocyanate as depicted in FIG. 8, can be used as a ligand to bind pathogens with similar surface chemistry. FIG. 8 illustrates a proposed route to surface immobilization of a carbohydrate (i.e., lactose) onto a surface-aminated substrate.

Disaccharide-Polyacrylamide Glycoconjugates

Figure 9A:
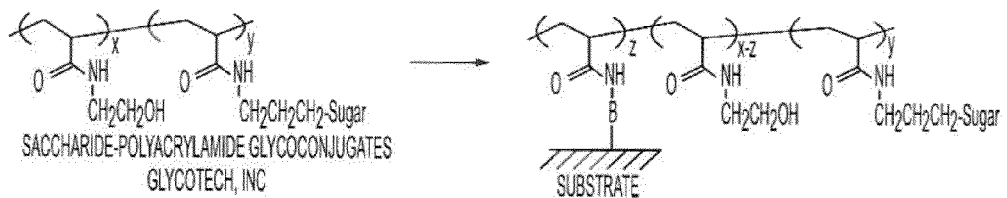
FIG. 9A-9C are schematics illustrating various reaction schemes for the surface immobilization of mono- and polysaccharide polyacrylamide glycoconjugates.
Figure 9B:
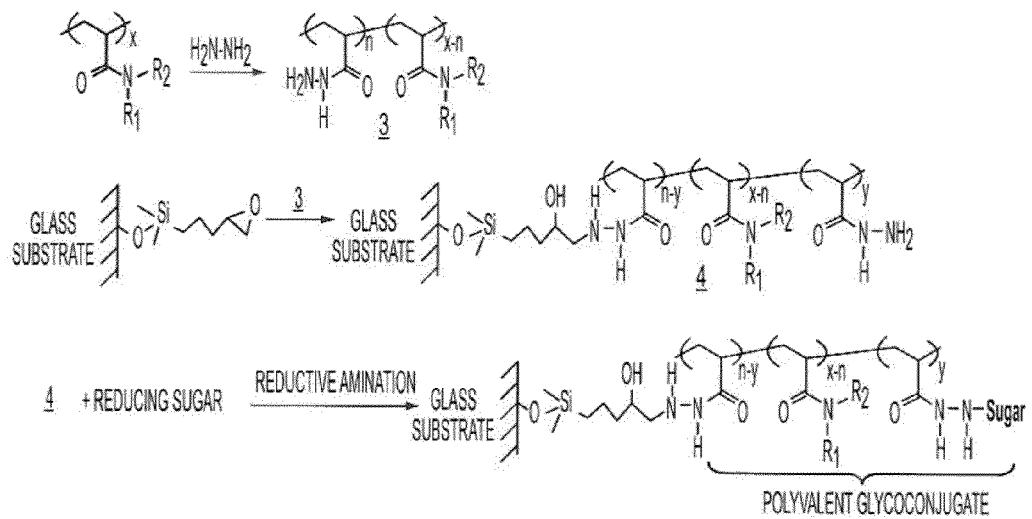
Figure 9C:
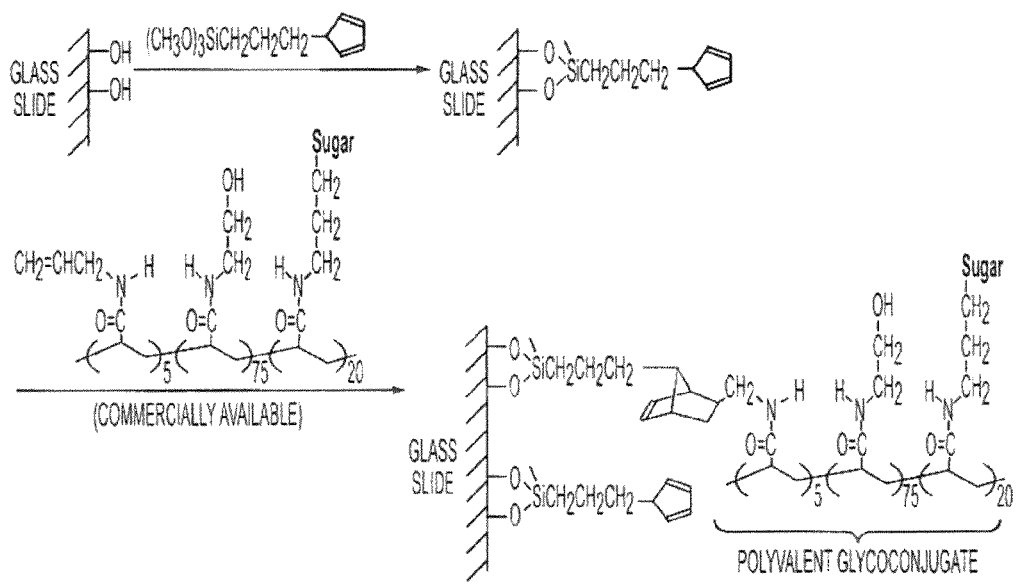

Multivalent disaccharide-polyacrylamide (Sugar-PAA) glycoconjugates can be used to bind and recognize *B. cereus, B. subtiles, B. pumilius,* and *thuringiensis* (Tarasenko et al., Carohydrate Res. 2004, 339, 2859-2870). The disaccharides include, but are not limited to, Galβ1-4Glcβ, Galα1-3GalNacα, Galβ1-3GalNacβ and Fucα1-4GlcNacβ. These glycoconjugates can be obtained from GlycoTech (Rockville, Md.). These disaccharide-polyacrylamide glycoconjugates can be immobilized on solid phases (Galanina et al., Spectrochim. Acta, Part A 2001, 57, 2285-2296). Surface-active substrates having a reactive linker (B) can be used for immobilization as depicted in FIG. 9A. FIG. 9A is a schematic illustrating a reaction scheme which can be used for the surface-immobilization of mono- and poly-saccharide polyacrylamide glycoconjugates. FIGS. 9B and 9C illustrate alternative reaction schemes for the surface immobilization of mono- and poly-saccharide polyacrylamide glycoconjugates. The silylated glass substrate can be prepared by exposing the glass surface to the vapor or solution of a silane (e.g., 3-glycidylpropyl trimethoxysilane as shown in FIG. 9B or 3-cyclopentadienylpropyl trimethoxysilane as shown in FIG. 9C. In FIG. 9B, $R_1$ and $R_2$ can be H or $CH_3$ independently and "Sugar" refers to a reducing sugar. Exemplary reducing sugars include mono-saccharides, di-saccharides, tri-saccharides and oligo-saccharides. The saccharide-polyacrylamide glycoconjugates include, but are not limited to, a-GalNAc-PAA, GlcNAcβ1-3Galβ-PAA, GlcNAcβ1-3(GlcNAcβ1-6)GalNAcα-PAA and GlcNAcβ1-3(GlcNAcβ1-6)GlcNAcβ1-6) GalNAcα-PAA.

Lectin-PEG Conjugates

As used herein, "PEG" or "poly(ethylene glycol)" refers to polymers containing recurring units derived from ethylene glycol (i.e., ethylene oxide recurring units). The terms "poly (ethylene glycol) (PEG) and poly(ethylene oxide) (PEO) are used interchangeably herein.

Figure 10:
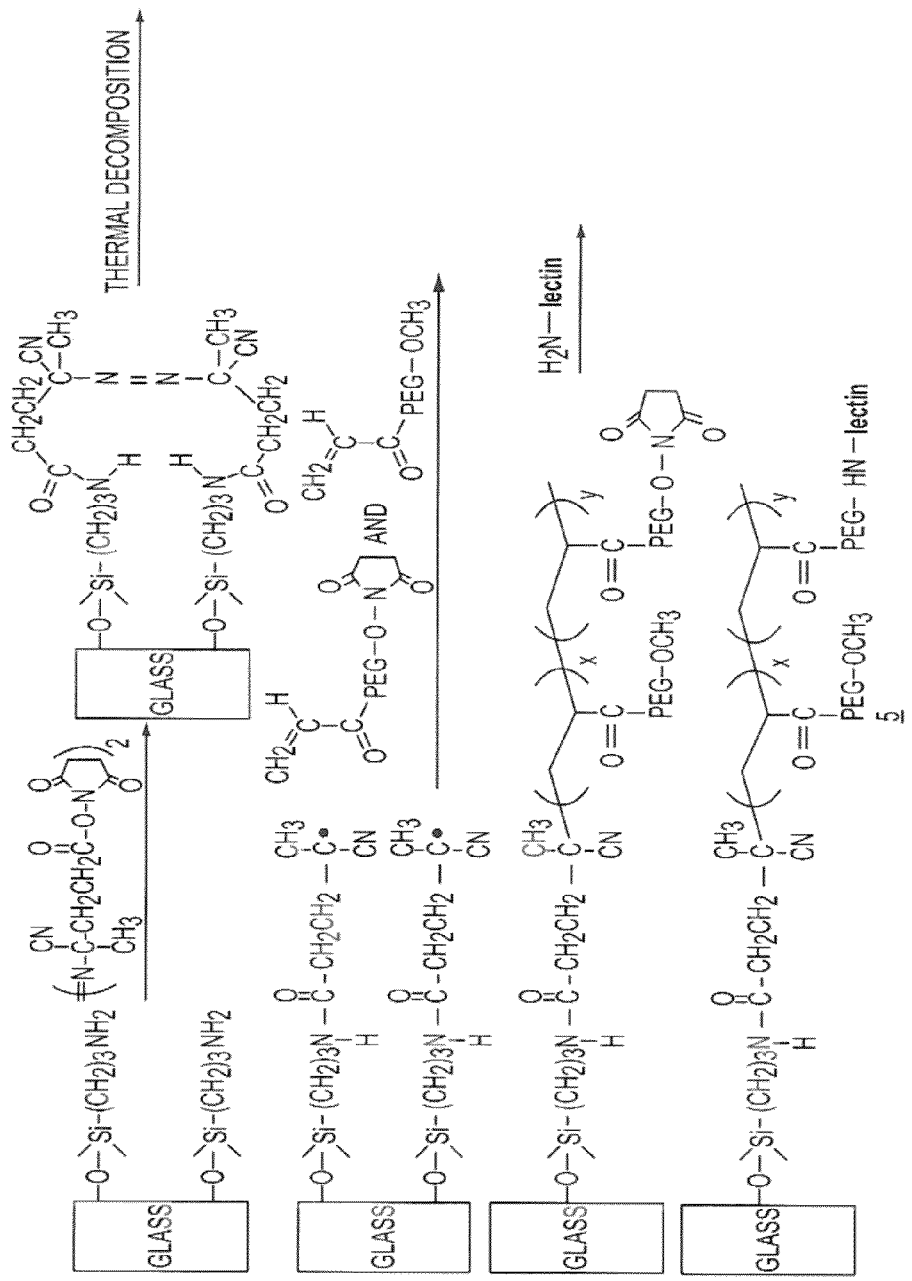
FIG. 10 is a reaction scheme for immobilizing lectin via reaction of its amino groups on a functionalized glass surface.

Lectins play important roles in the immune system by recognizing carbohydrates that are found exclusively on pathogens. *Helix Pomatia* lectin is known to have high affinity to *Bacillus thuriengiensis* (Levon et al., Macromol. Symp. 2003, 201, 114-117). Lectin can be immobilized onto a surface having n-hydroxy succinimide (NHS) activated carboxyl groups as depicted in FIG. 10. As shown in FIG. 10, an n-hydroxy succinimide/poly(ethylene glycol) (NHS-PEG) monomer is grafted onto a substrate by surface-initiated free radical polymerization to give multivalent conjugates (5) in the subsequent step. It is well known that multivalent conjugates have high affinity to target cells. It is reasonable to assume that any material having surface amino groups can be used as a substrate. The poly(ethylene glycol) (PEG) chains can be used to form a non-fouling surface resistant to non-specific adsorption of biomolecules such as proteins. Peptides and proteins containing terminal amino groups can be immobilized accordingly.

Carbohydrate-PEG Conjugates

Figure 11:
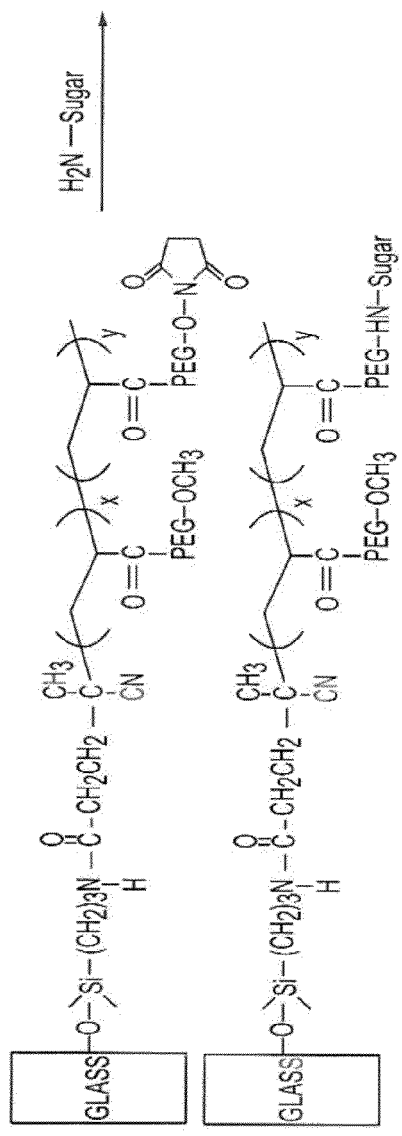
FIG. 11 is a reaction scheme for immobilizing sugar via poly(ethylene glycol) (PEG) chains on a glass surface.
Figure 12:
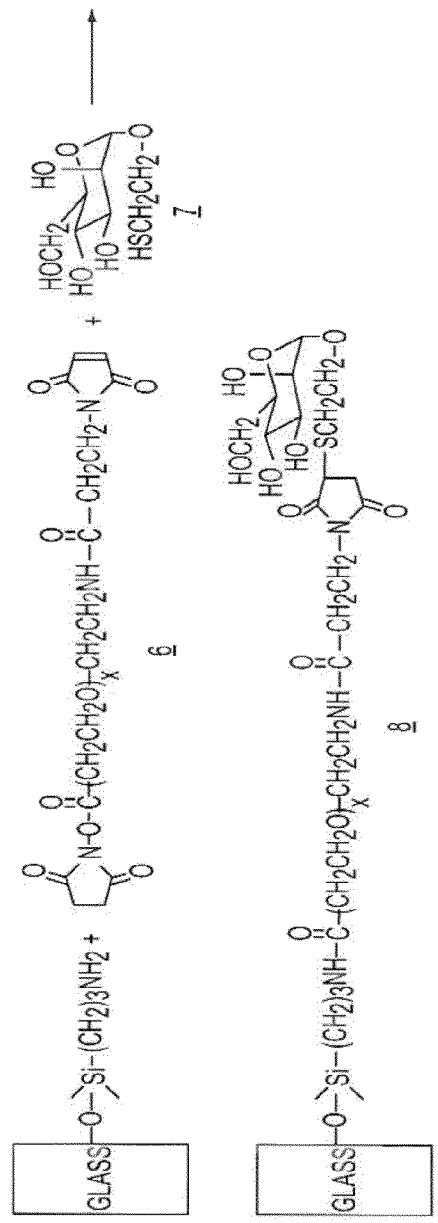
FIG. 12 is a reaction scheme for immobilizing a mannose-PEG conjugate on a glass surface.

As illustrated in FIG. 11, amino-sugars can be immobilized via PEG chains in a similar way as shown in FIG. 10. An alternative approach is depicted in FIG. 12 which is a schematic illustrating the immobilization of a mannose-PEG conjugate. This method involves the use of NHS-PEG-maleimide (6) (which can be obtained form Nektar, San Carlos, Calif.) and which can be conjugated to 2-mercaptoethyl α-D-mannopyranoside (2) (Houseman et al., Langmuir 2003, 19, 1522-1531) to prepare a monosaccharide-PEG conjugate (8).

Glycopeptide Conjugates

Figure 13:
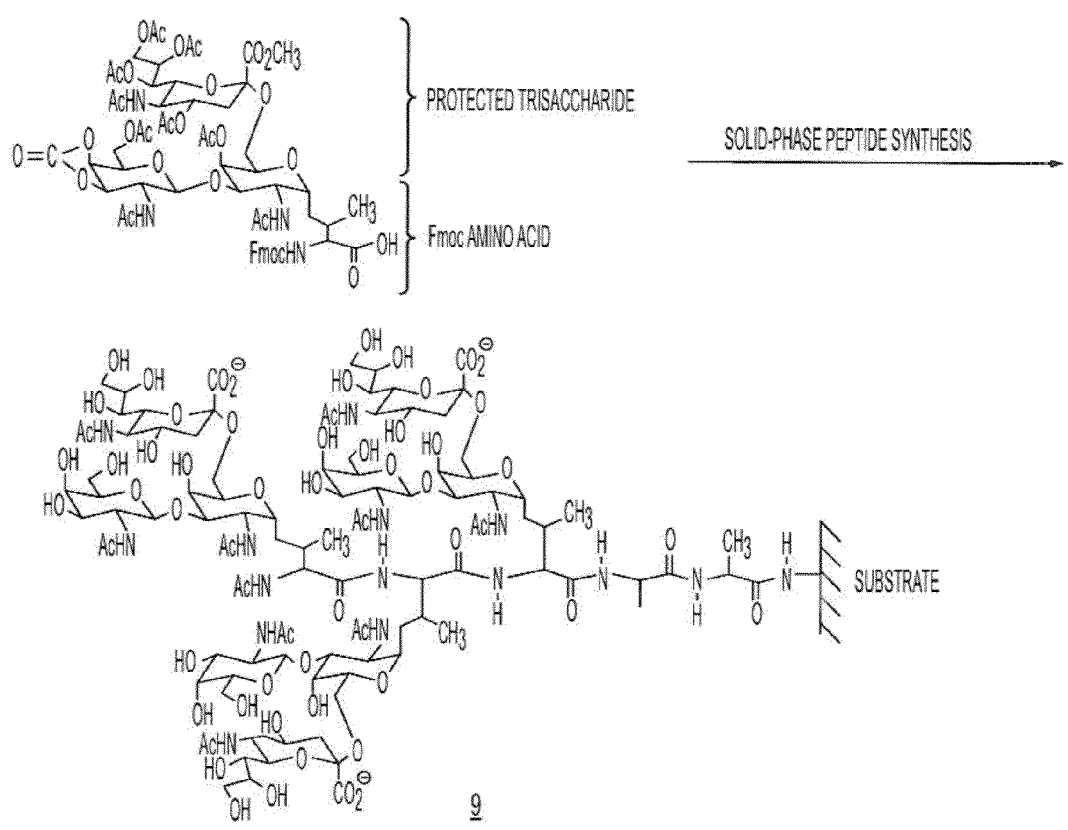
FIG. 13 is a reaction scheme for the synthesis of a glycopeptides by solid-phase peptide synthesis techniques.

Glycopeptide conjugates and their analogues can be synthesized en route solid-phase peptide synthesis similar to that reported by Sames et al., Nature 1997, 389, 587. FIG. 13 illustrates the synthesis of a glycopeptide (2) by solid-phase peptide synthesis. The solid support can be the same substrate onto which the conjugate is immobilized for pathogen detection.

Figure 14A:
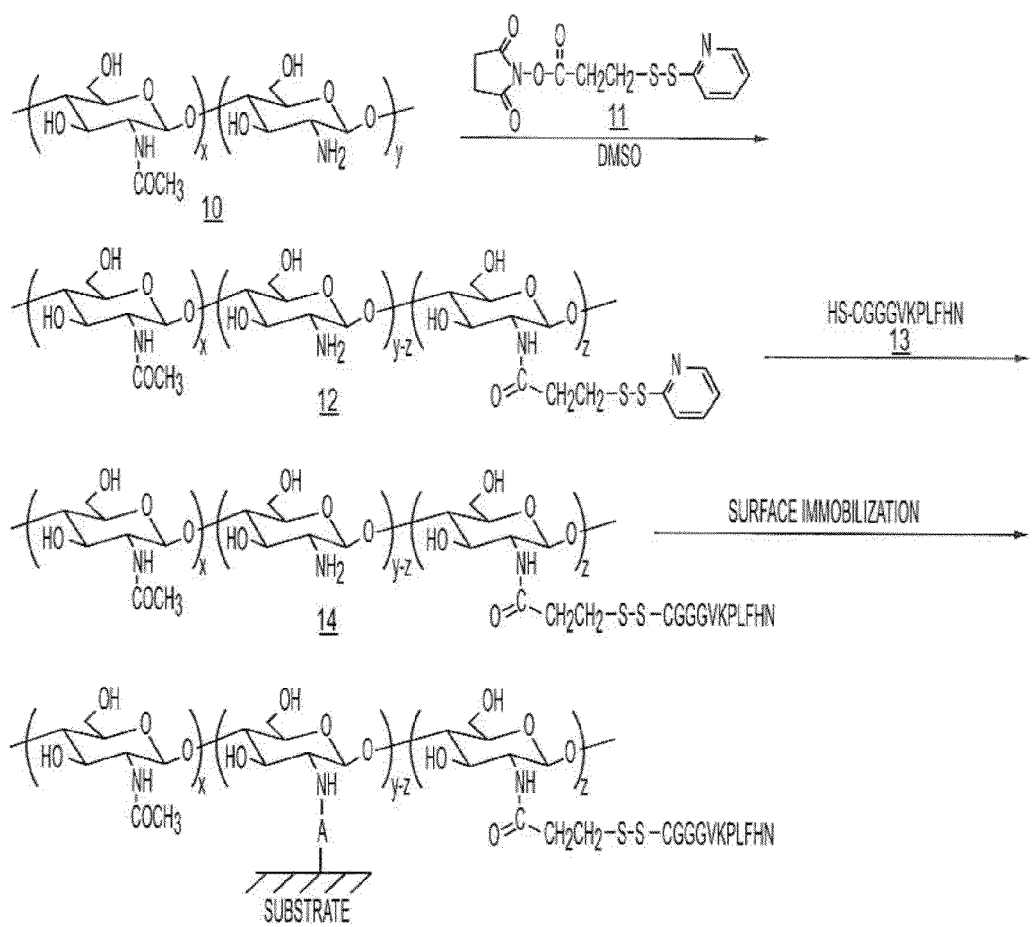
FIGS. 14A and 14B are schematics illustration reaction schemes for the synthesis and immobilization of *B. Subtilis* specific chitosan conjugate on a substrate.
Figure 14B:
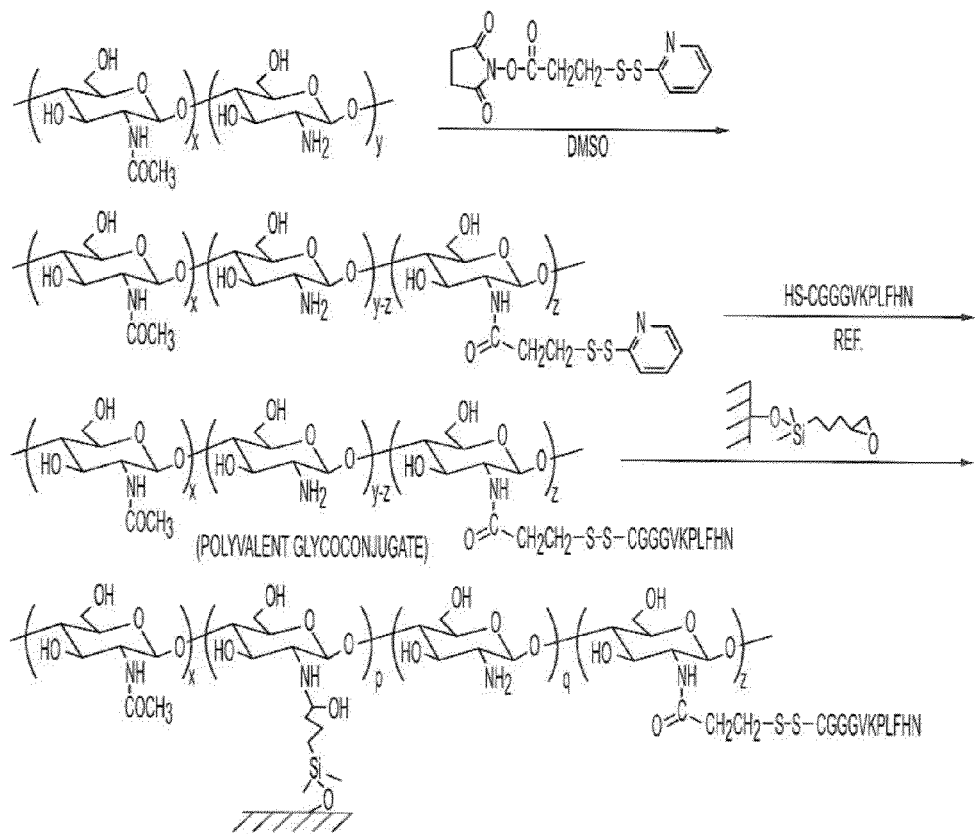

As illustrated in FIG. 14A, a *B. Subtilis* specific chitosan-peptide conjugate (14) can be synthesized by reacting activated chitosan (12) with *B. Subtilis* specific peptide (13) (Sharma et al., Polym. Prepr. 2002, 43, 736-737). Conjugate (14) may be immobilized onto the surface of a solid support having an reactive linker (A), for example, acetyl chloride or N-succinimidyl ester. FIG. 14B illustrates a similar reaction scheme involving surface immobilization via epoxy groups on the support surface.

Aptamers

Aptamers are oligonucleic acid or peptide molecules that bind a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. More specifically, aptamers can be classified as DNA or RNA aptamers which consist of (usually short) strands of oligonucleotides; peptide aptamers which consist of a short variable peptide domain, attached at both ends to a protein scaffold.

DNA or RNA aptamers are nucleic acid species that have been evolutionary engineered through/in vitro selection/or equivalently, SELEX (systematic evolution of ligands by exponential enrichment) to bind to various molecular targets such as small molecules, proteins, nucleic acids, and even cells, tissues and organisms. Aptamers offer the utility for biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which have good solubility and compacity properties. Currently, the bacterial protein Thioredoxin-A is the most used scaffold protein, the variable loop being inserted within the reducing active site, which is a -Cys-Gly-Pro-Cys- loop in the wild protein, the two Cysteins lateral chains being able to form a disulfide bridge. Peptide aptamer selection can be made using different systems, but the most used is currently the yeast two-hybrid system. The following references discuss aptamers: Ellington et al., "In vitro selection of RNA molecules that bind specific ligands", Nature, 1990 Aug., 30; 346(6287):818-22; Bock et al., "Selection Of Single-Stranded DNA Molecules That Bind And Inhibit Human Thrombin", Nature, 1992 Feb. 6, 355(6360):564-6; Hoppe-Seyler et al., "Peptide Aptamers: Powerful New Tools For Molecular Medicine", J. Mol. Med., 2000; 78(8):426-30; Carothers et al., "Informational Complexity And Functional Activity Of RNA Structures", J. Am. Chem. Soc., 2004 Apr. 28, 126(16):5130-7; Cohen et al., "An Artificial Cell-Cycle Inhibitor Isolated From A Combinatorial Library", PNAS, 1998 Nov. 24; 95(24): 14272-7; Binkowski et al., "Ligand Regulated Peptides: A General Approach For Selection Of Ligand Regulated Peptide-Protein Interactions," Chem. & Biol., 2005 Jul., 12 (7):847-55; Sullenger et al., "Emerging Clinical Applications Of RNA", Nature 2002, 418:252-258; and Ng et al., "Pegaptanib, A Targeted Anti-VEGF Aptamer For Ocular Vascular Disease," Nat. Rev. Drug Discov. 2006, 5:123-132.

The solid supports upon which the aptamers (e.g., peptide, DNA or RNA aptamers) are arrayed can be either glass slides or nylon membranes.

Lectins

Lectins are proteins that specifically interact with saccharides/carbohydrates. Lectins are found in a variety of species from plants to insects to man. They serve many different biological functions from the regulation of cell adhesion to glycoprotein synthesis and the control of protein levels in the blood. Lectins are also known to play important roles in the immune system by recognizing carbohydrates found exclusively on pathogens. According to some embodiments of the invention, lectins can be used as ligands (e.g., for the capture of glycoproteins or pathogens).

According to some embodiments, polyvalent macromolecules (e.g., polymers) comprising a plurality of ligands which specifically bind to a target analyte can be immobilized on the surface of the solid support in a discrete analyte binding area. The weight average molecular weights of the polyvalent macromolecules (polymers) can range from 100 to 5,000,000 Da, from 2000 to 2,000,000 Da, or from 10,000 to 1,000,000 Da.

The number of ligands in a macromolecule (polymer) can range from 1 to 500,000, from 100 to 50,000, or from 200 to 1,000. There can be two or more types of ligands in one macromolecule. For example, in one discrete area of an array, there can be one type of immobilized macromolecule comprising multiple ligands of one type, or multiple ligands of various types (two or more types of ligands). In addition, in one discrete area of an array, there can be various different immobilized macromolecules. For example, in one discrete area of an array, macromolecules having different backbones and/or architectures (e.g., linear, comb or hyperbranched polymers) each comprising multiple ligands of one type or multiple ligands of various types (e.g., two or more types of ligands) can be immobilized.

Bacterial cellular surfaces are littered with complex carbohydrate structures, such as glycoproteins, glycolipids, glycosaminoglycans, and proteoglycans. These glycoconjugates play a central role in cell-to-cell adhesion (binding) and subsequent recognition and receptor activation. However, the surfaces of different bacterial species can be chemically and morphologically quite distinct. Certain cells are able to selectively bind to one particular glycoconjugate but not to others. According to some embodiments, the special binding characteristics of the carbohydrate structures on the surface of the bacterial cell (e.g., polypeptides, carbohydrates, glycoconjugates, derivatives, and combinations thereof) can be used to detect pathogen cells without the need for DNA assays.

Reporters

The detection mode can vary depending on the nature of the reporter reagents. Exemplary detection modes include, but are not limited to, optical detection, electrochemical detection and electrical detection.

Optical Reporters

Various types of optical reporter reagents can be used for detection. For example, colloidal gold can be used for visual detection and/or visible spectrometery measurement. Conjugates of up-converting optical reporters which emit light in the visible spectrum when exposed to IR irradiation and ligands can also be used to visualize real time events and/or to improve specificity. Conjugates of quantum dot reporters and ligands can be used to visualize real time events and to improve specificity. Fluorescently labeled ligands can also be used for optical detection.

As set forth above, the reporter can be an up-converting reporter such as a phosphor which emits light in the visible spectrum when exposed to IR irradiation. Compared with a negative control, visible light emission upon IR radiation can be used to indicate the presence of target pathogens.

Figure 15A:
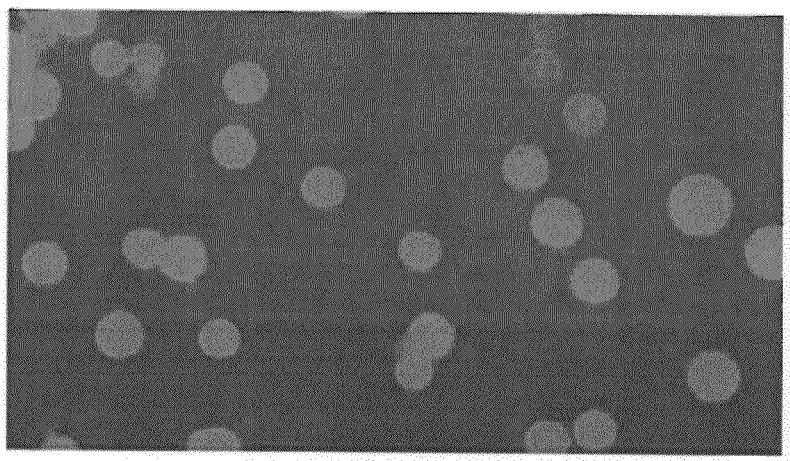
FIG. 15A is a photograph of a reporter comprising quantum-dots (Q-dots) dispersed in the matrix of an amine functionalized polyacrylamide bead.

The reporter can be an up-converting optical reporter such as a phosphor or a quantum dot. For example, the reporter can comprise quantum dots encapsulated in crosslinked polyacrylamide beads having surface amino groups for bioconjugation. A reporter of this type is shown in FIG. 15A. An exemplary polyacrylamide bead can have the following composition:

acrylamide 86.5 mole %;
methylenebisacrylamide 6.7 mole %; and
N-(3-aminopropyl)methacrylamide 6.8 mole %.

Figure 15B:
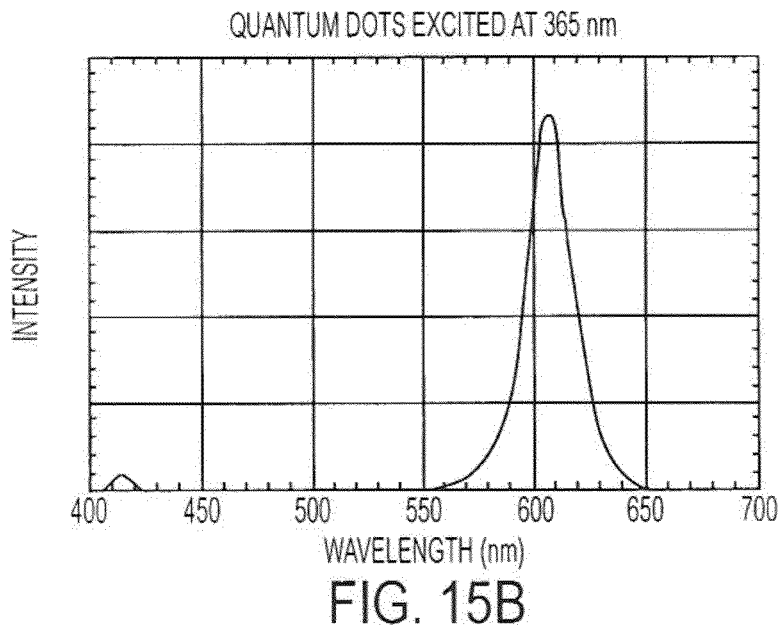
FIG. 15B is a graph of intensity as a function of wavelength for the quantum dots used in the reporter shown in FIG. 15A.
Figure 15C:
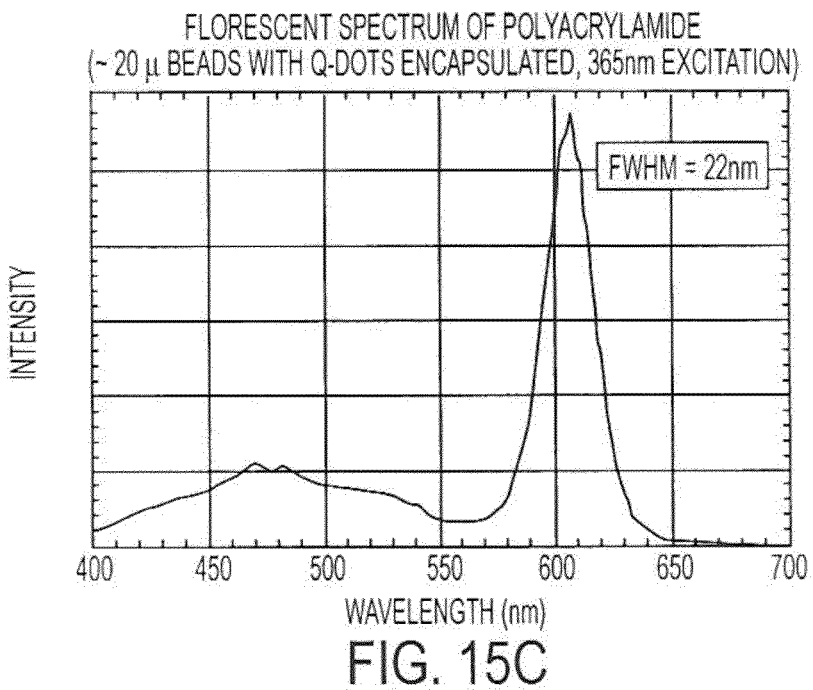
FIG. 15C is a graph of intensity as a function of wavelength for the reporter comprising polyacrylamide beads and quantum dots shown in FIG. 15A.

FIG. 15B is a graph of intensity as a function of wavelength for the quantum dots used in the reporter shown in FIG. 15A. FIG. 15C is a graph of intensity as a function of wavelength for the reporter comprising polyacrylamide beads and quantum dots shown in FIG. 15A.

The Q-dot concentration in the beads can be varied to provide desired detection characteristics. According to some embodiments, the Q-dot concentration in the beads can be $9.0 \times 10^{-7}$ M. Upon irradiation with infrared (IR) light, the up-converting reporters emit light in the visible spectrum. IR irradiation of the above described array after exposure to a plurality of pathogenic cells can thereby result in a recognizable or discernible pattern having specific characteristics indicative of the presence of a given target pathogen in the sample.

According to some embodiments, the reporter can also contain biotin molecules conjugated on its surface. For example, in the system and method set forth above which employs the magnetic capture of target analyte, the captured target pathogens with attached reporters and magnetic beads can subsequently be released by removing the magnetic field. The bead-pathogen-reporter-biotin complex as shown in step (c) of FIG. 4 can then be captured for a second time downstream by streptavidin immobilized on the surfaces of the cover and/or substrate. These complexes can then be detected (e.g., by exposure to IR radiation).

Figure 16A:
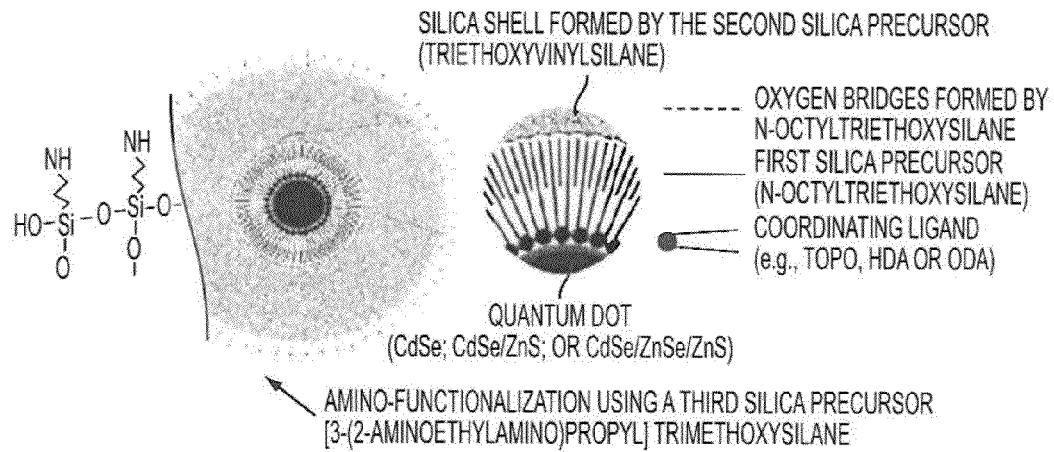
FIG. 16 is a schematic illustrating the immobilization of a polyvalent glycoconjugate to a surface modified Q-dot.
Figure 16B:
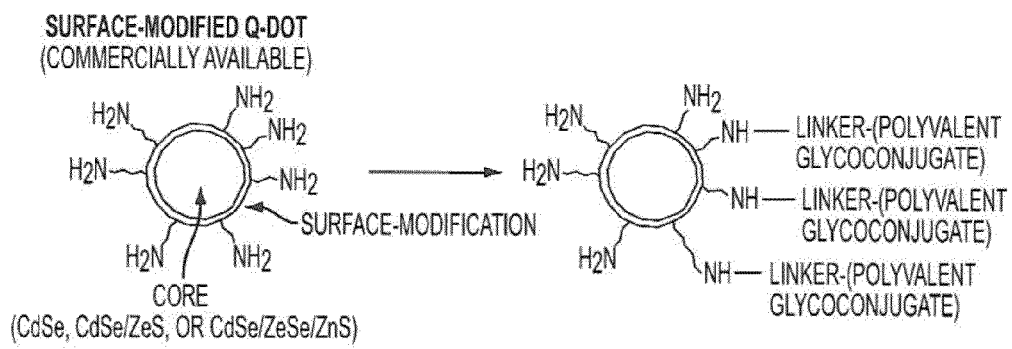
Figure 17A:
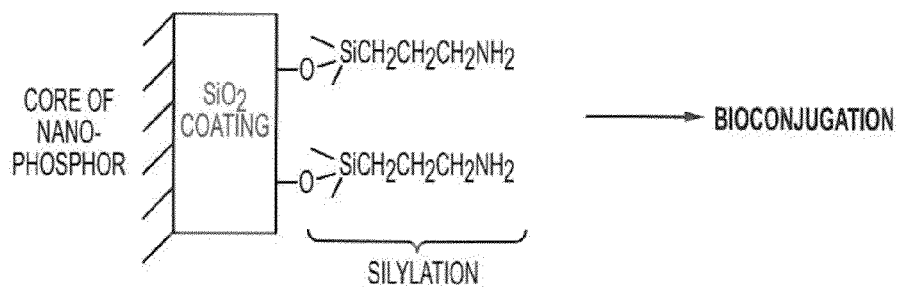
FIG. 17A is a schematic depicting the surface region of a surface amino-functionalized phosphor which can be used for bioconjugation.
Figure 17B:
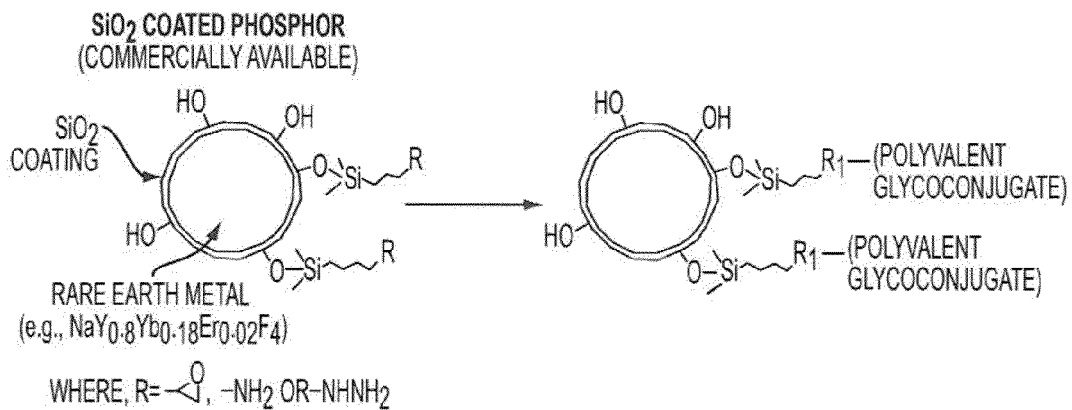
FIG. 17B is a schematic illustrating the immobilization of a polyvalent glycoconjugate to a $SiO_2$ coated phosphor.

Conjugates of up-converting optical reporters can be used to visualize real time events (e.g., calorimetry) and to improve specificity. The optical reporters can include lumiphores based on lanthanide complexes with an excitation wavelength of 300-340 nm and long lifetime emissions of 500-750 nm. Optical reporters of this type can be obtained from Lumiphore Technology (Redwood City, Calif.). The optical reporters can also include CdSe nanocrystals, quantum dots, which can be obtained from NANOCO Technologies Ltd. (Manchester, UK), Streptavidin-Qdot conjugates, which can be obtained from Invitrogen (Carlsbad, Calif.), surface-activated silica-shelled Qdots of the type disclosed in Balalova et al., Anal. Chem., ASAP Article 10.1021, Jul. 14, 2006, and surface-modified phosphors which can be obtained from Sunstone (Allentown, N.J.) and which are depicted in FIG. 17A. Through the surface functional groups of these optical reporters, ligands and other biomolecules can be attached covalently. The resulting conjugates can then be used as reporter reagents. A schematic depiction of covalent attachment of polyvalent glycoconjugates to a surface modified Q-dot is shown in FIG. 16. A schematic depiction of covalent attachment of polyvalent glycoconjugates to a $SiO_2$ coated phosphor is shown in FIG. 17B.

In various embodiments of the invention, the optical reporter can be an up-converting phosphor. Phosphors are made of a host material to which an activator (e.g., copper or bismuth) is added. Exemplary host materials include, but are not limited to, oxides, sulfides, elenides, halides or silicates of zinc, cadmium, manganese, aluminum, silicon, or various rare earth metals. Nanoparticles of phosphors having surfaces modified using silane chemistry are available from Sunstone Inc. (Allentown, N.J.). An exemplary schematic of a surface functionalized phosphor of this type having amino functional groups on the surface is shown in FIG. 17. Although amino groups are depicted in FIG. 17, the surface of the phosphor may be modified to include other surface functional groups for bioconjugation including carboxylic acid groups. The surface functional groups (e.g., amino or carboxylic acid groups) of these nano-phosphor particles can be used for bioconjugation of biomolecules. The resulting bioconjugates can be used as reporter reagents wherein the biomolecule specifically binds to a pathogen.

Figure 18:
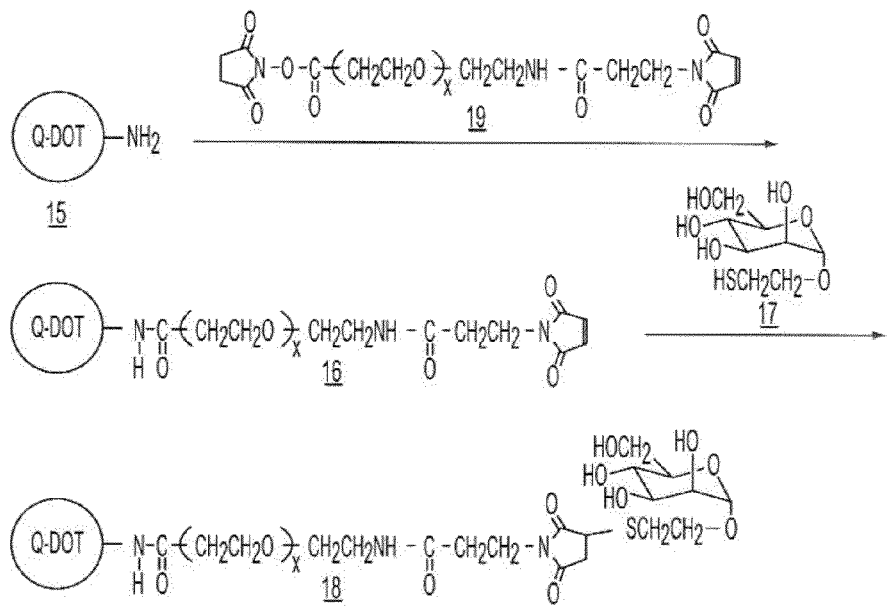
FIG. 18 illustrates a reaction scheme for the preparation of quantum dot reporters containing sugar ligands which can be used to bind pathogen cells.

In various embodiments of this invention, ligand-derivatized reporters having optical labels can be prepared using aminated quantum dots (i.e., Q-dots) which can be obtained from Invitrogen. As depicted in FIG. 18, aminated Q-dots (15) can be reacted with telechelic poly(ethylene oxide) (19) to yield maleiamide-derivatized Q-dots (16) that can be reacted with a thiolated sugar (17) in a subsequent step to give a sugar-derivatized reporter (18). The reporter (18) can bind and visualize pathogen cells that have been captured previously (e.g., on the sugar-derivatized glass surface or gold arrays as described above).

Electrochemical Reporters

Electrochemical reporters can also be used. Two different schemes for electrochemical detection can be used in the above described methods and systems. The first involves capturing the analyte at an electrode through direct ligand capture or magnetic capture and allowing an electrochemically labeled ligand to bind to the captured analyte. Electrochemical labels may include electrocatalytic mediators that would allow signal amplification utilizing a sacrificial substrate to achieve the necessary sensitivity. The analyte can be a cell (e.g., a pathogenic cell) in which case the electrochemically labeled ligand can bind to the outside surface of the captured cell.

The second scheme can be used when the analyte is a cell and involves the specific capture of the analyte cells upstream of an electrode in a flow system. The analyte cells can then be lysed and the lysis products detected downstream at a modified electrode. Modification of an electrode surface with a catalytic mediator such as tris-(bipyridine) ruthenium would allow detection of the cell lysate as it flows over the electrode. This mediator allows efficient catalytic oxidation of various molecular components of the cell such as quanine derivatives and various amino acids such as tyrosine. This scheme should allow for very sensitive detection of whole cells.

Substrates

Some examples of substrates (i.e., solid supports) that can be used include, but are not limited to, mica, silica, glass, quartz, indium tin oxide (ITO), alumina, and polymers, for example, PDMS, PMMA, PET, polycarbonate, and PS. The substrate can have innate functional groups on the surfaces or can be surface-functionalized to carry functional groups for immobilization of bioconjugates/glycoconjugates. The functional groups include, but are not limited to, alkynyl, dienyl, amino, azide, hydrizide, carboxylic, acid anhydride, aldehyde, ketone, isocyanate, thioisocyanate, ester, N-succinimido ester (NHS), borate, maleimide, disulfide and mercapto groups.

Figure 19A:
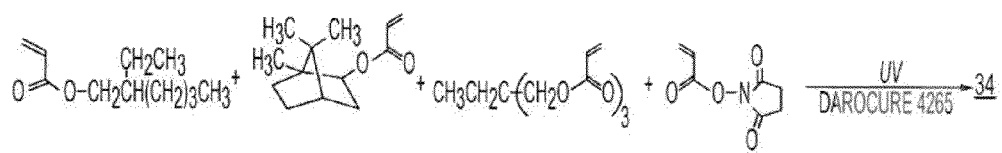
FIG. 19A is a reaction scheme for the synthesis of a macroporous polymer monolith containing surface N-hydroxysuccinimide (NHS) groups.
Figure 19B:
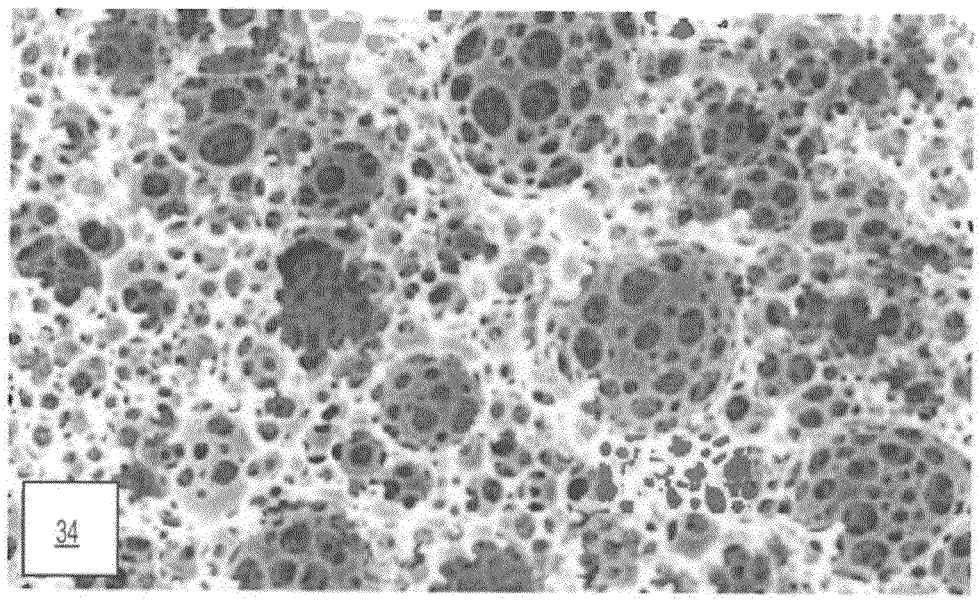
FIG. 19B is a picture of a cross-section of the macroporous polymer monolith containing surface N-hydroxysuccinamide (NHS) groups made by the reaction scheme of FIG. 19A.
Figure 20:
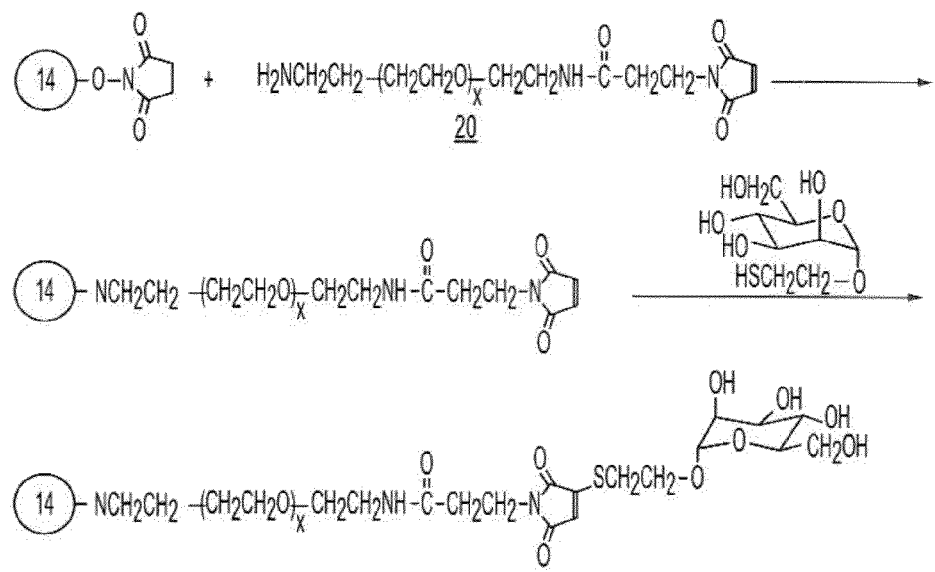
FIG. 20 is a reaction scheme for immobilizing a monosaccharide on a PEGylated surface of the porous polymer monolith made by the reaction scheme of FIG. 19A.

The substrate can also be a porous polymer monolith having surface-NHS for immobilizing conjugates. A method of making a porous polymer monolith having surface-NHS which can be used to immobilize ligands is shown in FIGS. 19A and 19B. FIG. 19A is a reaction scheme for the synthesis of a macroporous polymer monolith (34) containing surface N-hydroxysuccinimide (NHS) groups. FIG. 19B is a picture of a cross-section of the macroporous polymer monolith containing surface N-hydroxysuccinamide (NHS) groups (34) made by the reaction scheme of FIG. 19A. The porous polymer monolith can be prepared by High Internal Phase Emulsion Polymerization (HIPE) as reported by Thies et al., Polym. Prepr. 2005, 46, 1235-1236 and European Patent Publication No. 299762 (1989). Other suitable substrates include noble metals, synthetic membranes and nitrocellulose membranes. The surface of the porous polymer monolith can be PEGylated as illustrated in FIG. 20. In FIG. 20, "x" is 0 or a positive integer. As also shown in FIG. 20, an amino-PEG-maleimide linker (20) can be used to anchor a ligand (e.g., α-D-mannopyranoside) onto the surface of the surface-PEGylated porous polymer monolith. The PEG chains on the surface of the porous polymer monolith can form a non-fouling surface resistant to non-specific adsorption of biomolecules such as proteins.

Figure 21:
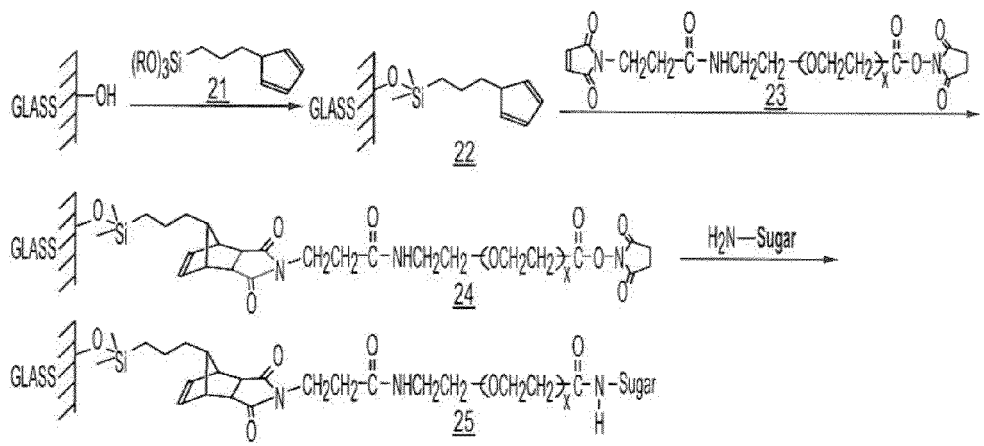
FIG. 21 illustrates a reaction scheme for immobilizing sugar moieties on a surface of a glass substrate.

As set forth above, the substrate can be glass. According to some embodiments, a sugar moiety (e.g., a monosaccharide, a disaccharide, a trisaccharide, an oligosaccharide or a polysaccharide) can be immobilized onto a glass surface via a Diels-Alder reaction as illustrated in FIG. 21. In FIG. 21, "x" is 0 or a positive integer. As shown in FIG. 21, surface silanol groups on a glass substrate can be reacted with 3-(1-cyclopentadienyl) propyltrialkoxysilane (21), which can be obtained from Gelest, to give compound (22) which, in turn, can be reacted with MAL-PEGx-NHS (23), which can be obtained from Quanta Biodesign, via Diels-Alder addition reaction to give an NHS-functionalized surface (24). Sugar molecules can then be immobilized onto the surface by reacting the surface NHS groups with an amino-sugar to give (25).

Figure 22:
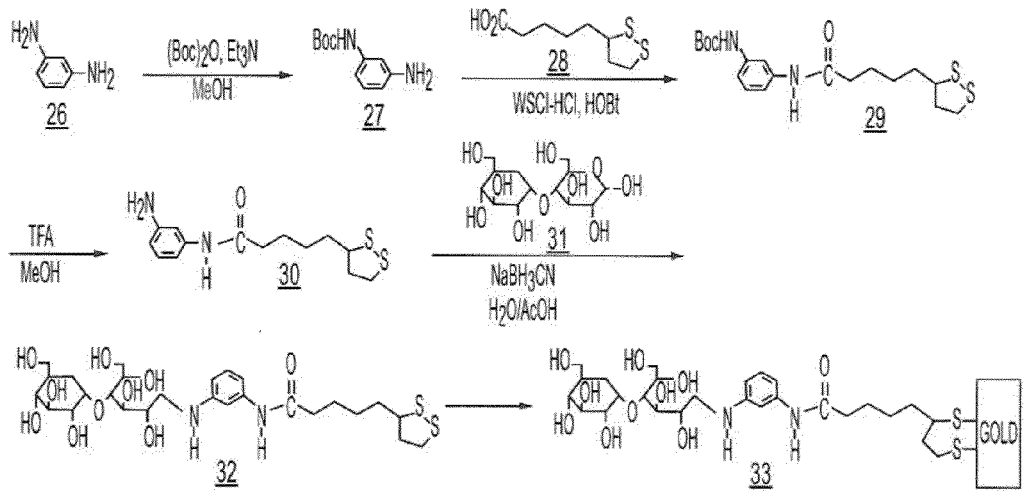
FIG. 22 illustrates a reaction scheme for immobilizing sugar moieties on a surface comprising gold.

In various embodiments, sugar molecules can be surface-immobilized onto arrays of gold electrodes as depicted in FIG. 22. In FIG. 22, "HOBt" refers to hydroxybenzotriazole. As shown in FIG. 22, reaction of 1,3-phenylenediamine (26) with di-t-butyldicarbonate in methanol yields 3-(t-butoxycarbonylamino)phenylamine (27) which in turn can be reacted with thiotic acid (28) to give amide derivative (29). Compound (29) is then treated with trifluoroacetic acid to give linker compound (30) which undergoes reductive amination reaction (Birch reduction) with a reducing sugar such as, for example, D-maltose (31), to give D-glucopyranoside-containing ligand conjugate (32). Ligand conjugate (32) is capable of immobilizing itself on the surface of a gold surface to form surface immobilized compound (33). Other reducing sugars can be immobilized on gold arrays in a similar manner.

The above described devices can be used for direct analysis of target analytes without sample pre-treatment or sample preparation by applying and integrating the well-known principles of physics, chemistry, biochemistry, and biology. The devices and methods allow for the direct measurement of pathogenic organisms without the need for sample preparation (e.g. for biological samples) and PCR. The small dimensions and simplicity of the proposed technology enable highly mobile deployment in the widest variety of settings (e.g. handheld devices, stationary devices containing target specific probes, etc.).

The systems and methods described herein enable the enrichment of rare malignant cells from patient samples and can aid in the diagnosis, prognosis, and development of therapeutic modalities for patients. Additional advantages include: (1) cost effectiveness; (2) a user friendly format; and (3) potentially fast detection (e.g., in minutes). The devices can be used for point-of-use environment detection, point-of care diagnostics, and immunoassays for drug development.

Applications include devices designed to be used individually as a point-of-use sensor for airborne pathogens, and other pathogenic organisms in foods and agriculture produces. The devices can also be used as a centennial sensor for a surveillance system that comprises a Taqman probe DNA analyzer to be deployed for infectious disease detection.

EXAMPLES

Aspects of the present teachings may be further understood in light of the following examples, which should not be construed as limiting the scope of the present teachings in any way.

FITC-Lectins Assay on Monosaccharide Array

Figure 23:
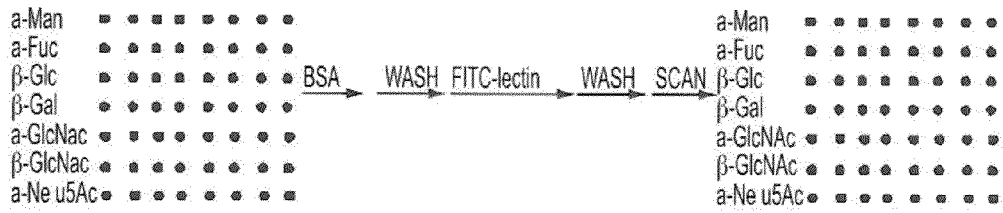
FIG. 23 is schematic illustrating a reaction scheme for an assay for lectins conjugated to fluorescein isothiocyanate (i.e., FITC-lectins) using a monosaccharide array.
Figure 24:
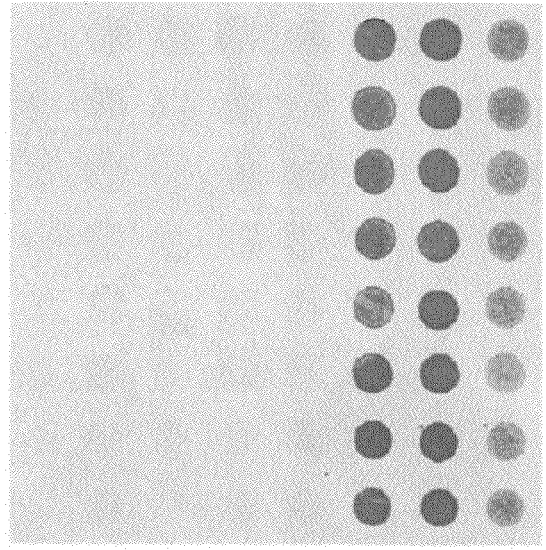
FIG. 24 is a photograph of a monosaccharide array on which an assay was conducted for FITC-lectin *Triticum vulgaris* (wheat).
Figure 25:
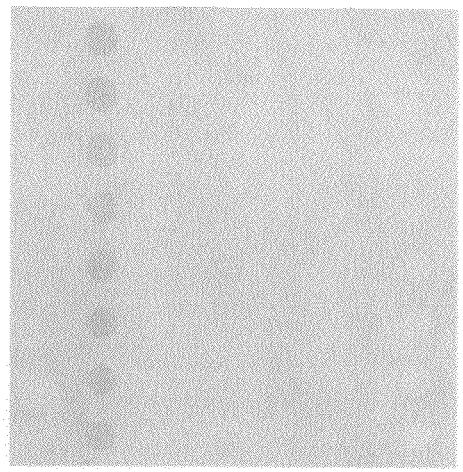
FIG. 25 is a photograph of a monosaccharide array on which an assay was conducted for FITC-lectin *Lens culinaris* (lentil).

The monosaccharide arrays prepared according to FIG. 9C were used for the assay. The lectin samples were labeled with fluorescent isothiocyanate (FITC) obtained from Sigma. The reaction scheme for this assay is depicted in FIG. 23. The assay results are shown in FIGS. 24 and 25.

Materials

FITC-lectin *Triticum vulgaris* (wheat), Sigma L4895 (alpha and beta-GlcNAc specific)

FITC-lectin *Lens culinaris* (lentil), Sigma L9262 (alpha-man specific)

Assay Procedure

The arrays prepared according to FIG. 9C were treated with bovine serum albumin (BSA) (3 mg/ml) in phosphate buffered saline (PBS) for 30 minutes and washed three times with PBS and last with doubly distilled (dd) water before they were blow dried.

Make FITC-lectin solution (20 ug/ml) in PBS with 0.2% Tween 20.

Applied 200 µl of the FITC-lectin solution and covered with cover slide, incubated for 1 hour at room temperature (RT).

The slides were washed five times with PBS (0.2% Tween 20) and last with dd water before they were blow dried.

The slides were scanned on a Typhoon scanner (Fullmoon Biosystems, Sunnyvale, Calif.) with excitation wavelength at 488 nm, PMT 600, resolution 50 µm, and medium sensitivity.

Results and Observation

Both vapor silanated and solution silanated slides worked well. Control clean bare slides had low signal and high background.

Both lectins showed specific binding toward their ligands.

FITC-lectin *Triticum vulgaris* (wheat) has stronger affinity than FITC-lectin *Lens culinaris* (lentil) toward their ligands in this format.

Reference

S. Park, M. Lee, S. Pyo, and I. Shin J. Am. Chem. Soc. 2004, 126, 4812-4819

Pathogen Cell Assay on a Monosaccharide Array

Figure 26:
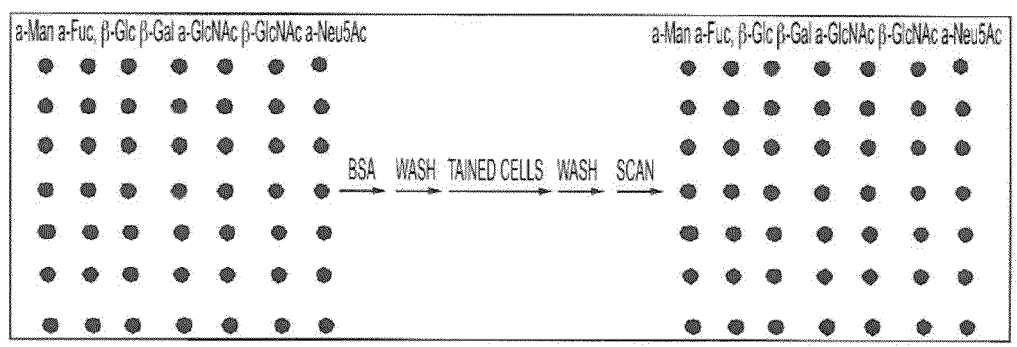
FIG. 26 is a schematic depicting the reaction scheme for a pathogen cell assay on a monosaccharide array.
Figure 27A:
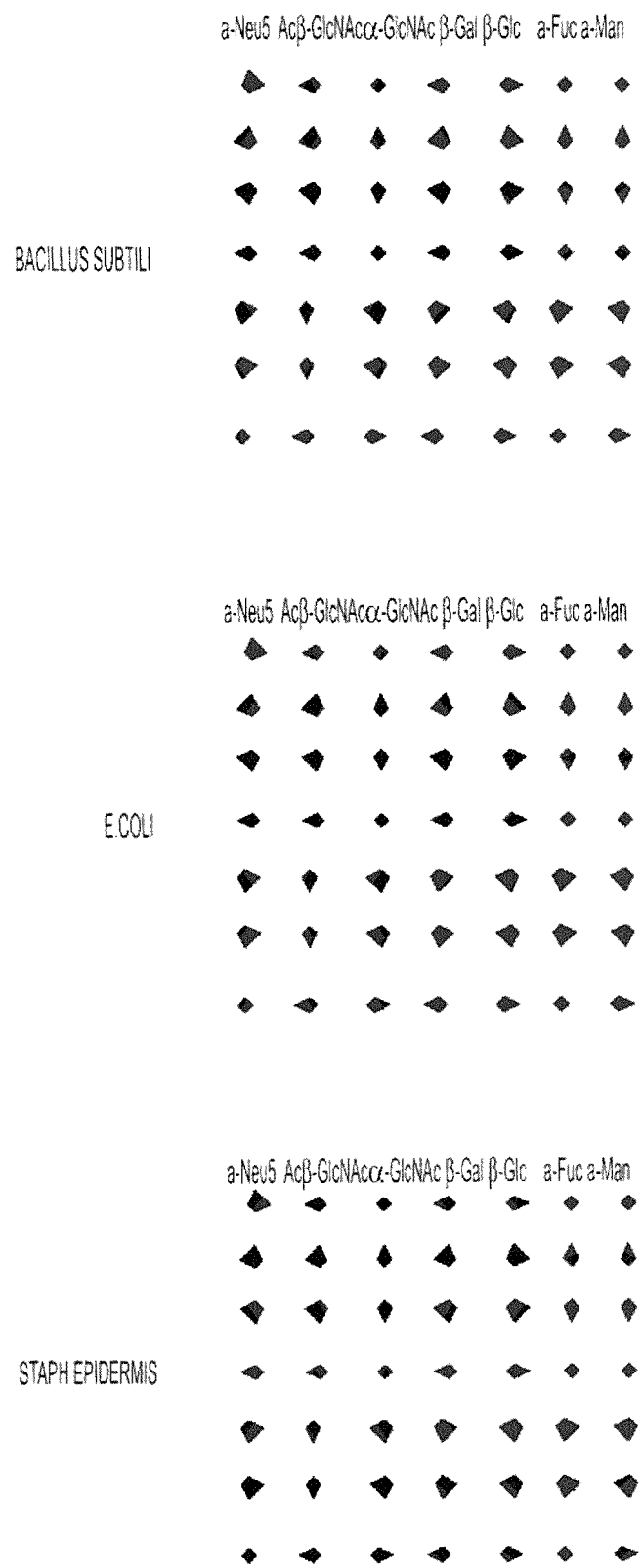
FIG. 27 is a schematic depicting the array layout for a pathogen cell assay on a monosaccharide array.
Figure 27B:
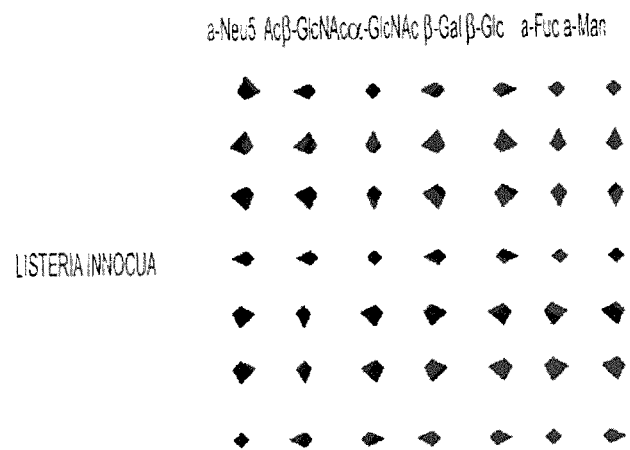
Figure 27B:
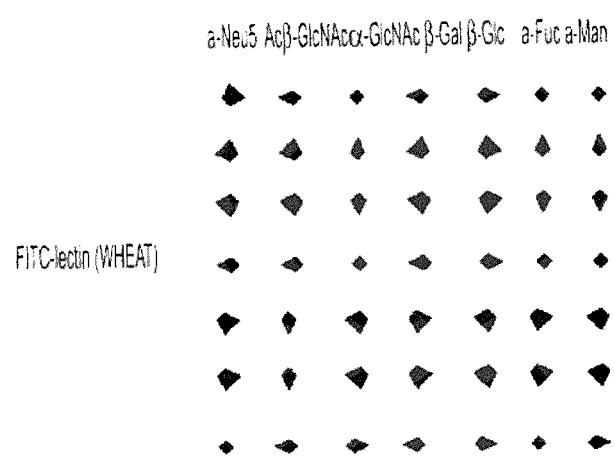
Figure 27B:
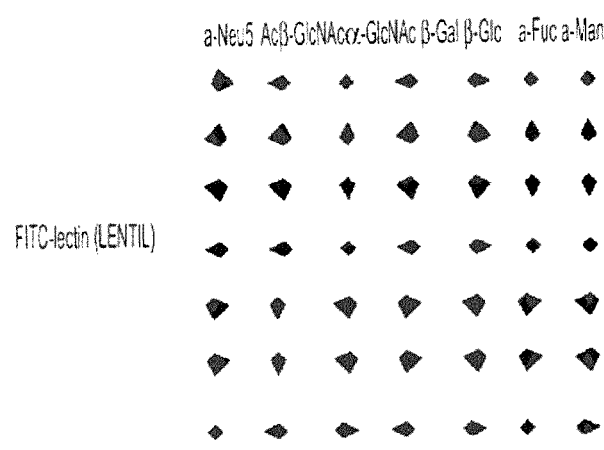
Figure 28A:
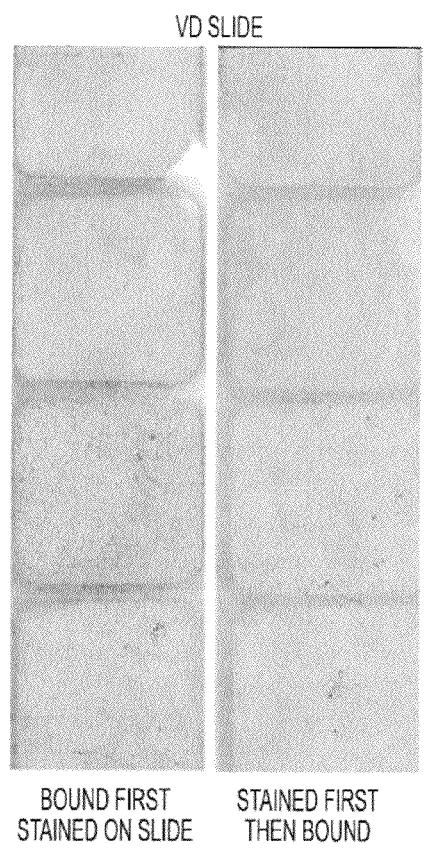
FIGS. 28A and 28B are photographs of (VD) cyclopentadiene slides and nitrocellulose slides, respectively, on which pathogen cell assays for four different pathogens (*Bacillus subtili, E. Coli, Staph Epidermis* and *Listeria Innocula*) were conducted comparing assays wherein the cell was bound before staining with those where the cell was bound after staining.
Figure 28B:
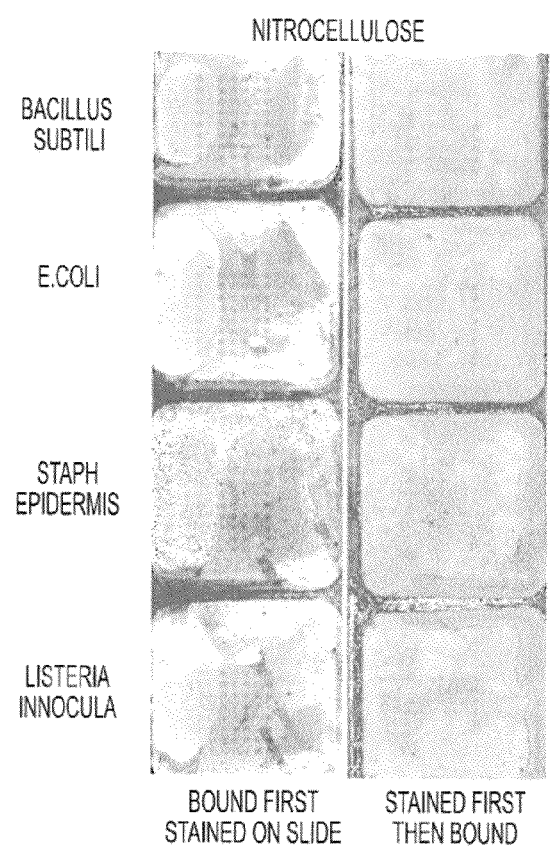

The monosaccharide arrays prepared according to FIG. 9C were used for the assay. The reaction scheme for this assay is depicted in FIG. 26 and the array layout in FIG. 27. The assay results are shown in FIGS. 28A and 28B.

Materials

FITC-lectin *Triticum vulgaris* (wheat), Sigma L4895 (alpha and beta-GlcNAc specific)

FITC-lectin *Lens culinaris* (lentil), Sigma L9262 (alpha-man specific)

Vybrant dye Cycle Green stain 5 mM in dimethylsulfoxide (DMSO) (V35004, Invitrogen)

Pathogen cells: cultistik *Bacillus Subtili* (29446-606), kwik-stik *E. Coli* (2449-074), *Listeria Innocua* (29450-126), kwik-stik *Staph Epidermis* (29446-524)

Arrays were spotted on both cyclopentadiene slides (VD slides) and nitrocellulose slide (Fullmoon Biosystems type C slides).

Procedure

Spotting

Spotting solutions: 10 mg/ml of the sugar concentrate in dd water (yellowish clear solution). Use pipette tips to hand spot approximately 0.1 ul per spot. The spotted slides which had been previously surface treated with a solution of 3-cyclopentadienylpropyltriethoxysilane, were placed in a humidity chamber (pure water reservoir) at room temperature for 16 hours (overnight). The slides were soaked in dd water for three hour. The slides were sonicated in dd water for 5 minutes. The slides were rinsed with dd water, dried with $N_2$ gun and ready for assay.

Reference

Wang, "Carbohydrate Microarrays," *Proteomics* 2003, 3, 2167-2175.

Cell Cultures

The cells were suspended in PBS with 0.2% Tween 20 and innoculated on an Agar petri dish and incubated at 37° C. overnight. *E. coli* on LB agar, all other on BBL® trypticase soy agar (TSA).

The cells were harvested and suspended in PBS. OD 600 was measured to quantitate cell concentrations. The concentrations were as follows:

*Bacillus Subtili:* 0.23;
*E. Coli:* 0.57;
*Listeria Innocula:* 0.17; and
*Staph Epidermis:* 0.33.

Cell Staining

The cells were diluted to 0.01 OD (by calculation, $10^7$ cells/ml) and then stained with Vybrant dye: 2 μl dye was added to 1 ml of the cells in PBS with 0.2% Tween 20 and incubated at 37° C. for 1 hour.

Make FITC-lectin solution (20 ug/ml) in PBS with 0.2% Tween 20.

Blocking Slides

Before conducting the assay, the slides were blocked by treating with BSA (3 mg/ml) in PBS for 30 minutes and washed three times with PBS and last with dd water before they were blow-dried.

Assay

Applied 50 μl of the stained or unstained cell suspension or FITC-lectin solution to respective array block with a gasket and covered with cover slide, incubated for 1 hour at RT.

With the unstained cell binding, the dye was applied on slide and incubate for 1 hr to stain cells on slides.

The slides were washed five times with PBS 0.2% Tween 20 and last with dd water before they were blow-dried.

Scanning

The slides were scanned on a Typhoon scanner (Fullmoon Biosystems, Sunnyvale, Calif.) with excitation wavelength at 488 nm, PMT 600, resolution 50 μm, and medium sensitivity.

Results and Observation

Control FITC-lectin binding was observed. Stained cells bound to the immobilized sugar ligand.

Nitrocellulose slides gave relatively higher signal to noise ratio.

Cell binding was positive.

Reference

Disney et al., Chemistry & Biology, Vol. 11, 1701-1707, December, 2004.

Maleimide PEG (mPEG-MAL) to Reduce Background Noise

Figure 29:
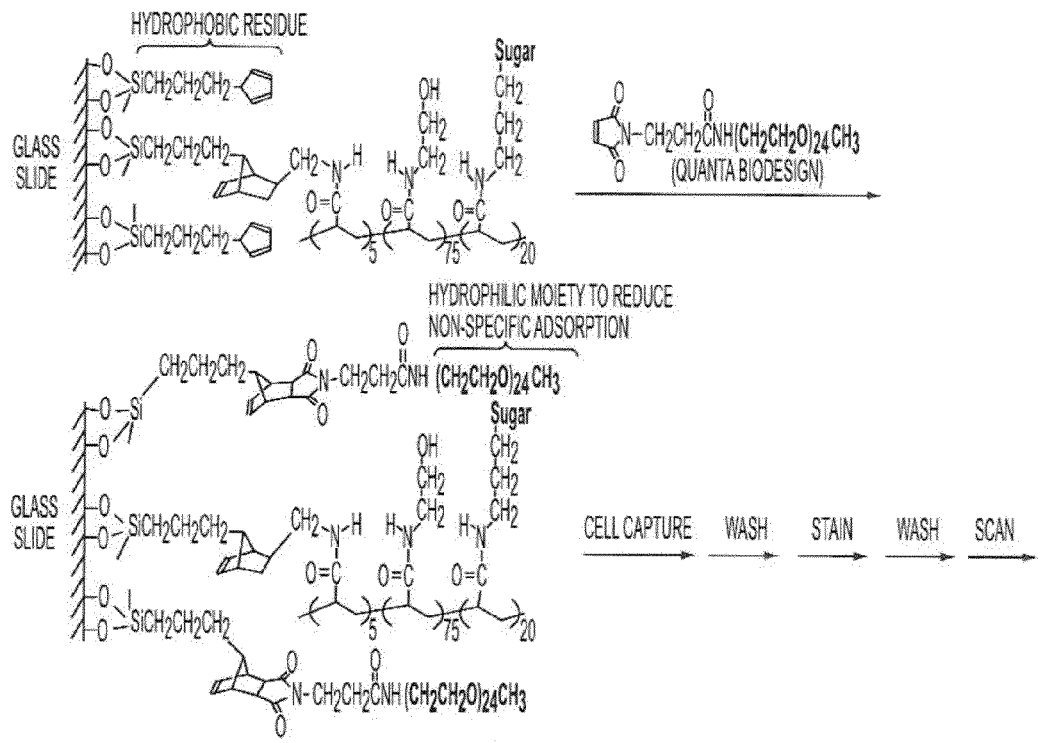
FIG. 29 is the reaction scheme for a pathogen cell assay using a monosaccharide array wherein the array is on a maleimide PEG (mPEG-MAL) treated cyclopentadiene surface.

Unreacted surface cyclopentadiene groups create hydrophobic domains that encourage non-specific adsorption of fluorescent dye resulting in relatively high background noise. As shown by the reaction scheme of FIG. 29, maleimide PEG (mPEG-MAL) can be used to block a cyclopentadiene surface using a Diels-Alder reaction.

Spotting

Spotting solutions: 10 mg/ml of the sugar conjugate in dd water (yellowish clear solution).

Use pipette tips to hand spot approximately 0.1 ul per spot.

Slides: Glass slides had been previously surface treated with a solution of 3-cyclopentadienylpropyltriethoxysilane.

The spotted slides were placed in a humidity chamber (pure water reservoir) at room temperature for 16 hours (overnight).

The slides were soaked in dd water for three hour.

The slides were sonicated in dd water for 5 minutes.

The slides were rinsed with dd water, dried with $N_2$ gun and ready for assay.

Figure 30:
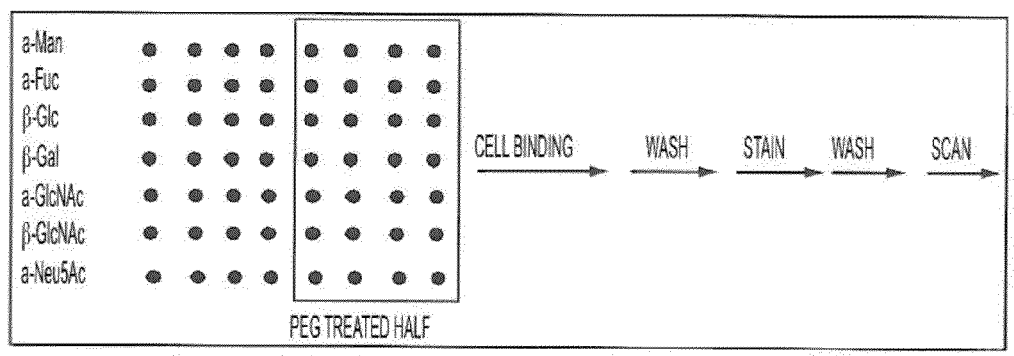
FIG. 30 is a schematic illustrating the reaction scheme involving the use of maleimide PEG (mPEG-MAL) to block a cyclopentadiene surface to reduce background of sugar array slides using a Diels Alder reaction.
Figures 31, 32:
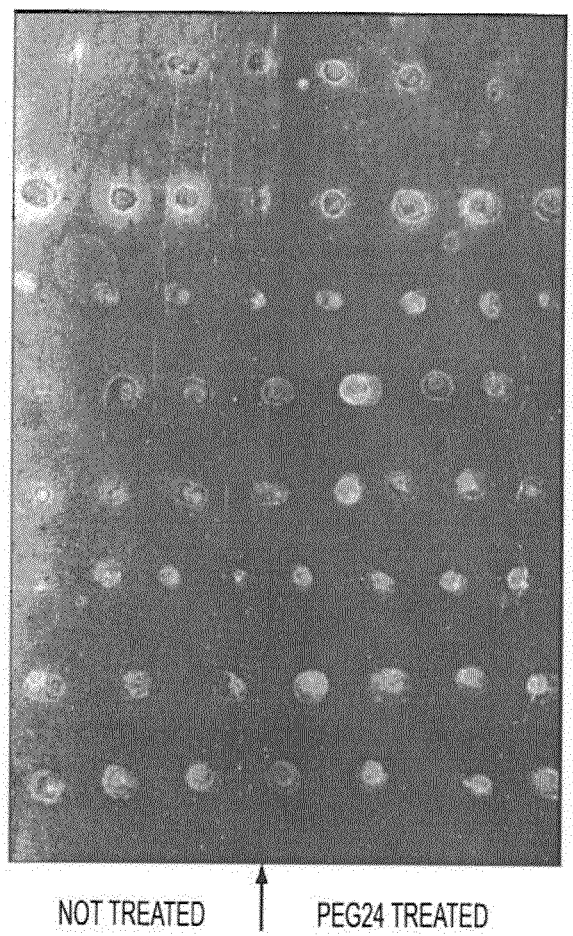
FIG. 31 is a spotting pattern for an assay using the mPEG-MAL blocked cyclopentadiene surface sugar array slides made by the reaction scheme of FIG. 42.
FIG. 32 is a scanned image of a pathogen assay for S03 *Bacillus subtili* cells using a monosaccharide array wherein half of the array has been treated with maleimide PEG (mPEG-MAL) to cap the residual cyclopentadiene groups as depicted in FIG. 29.
Figure 33:
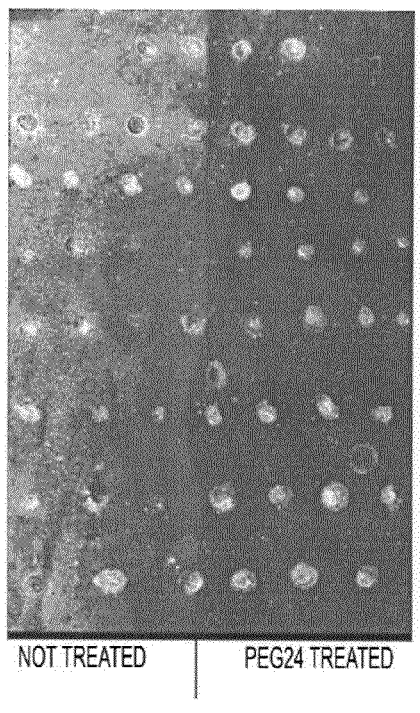
FIG. 33 is a scanned image of a pathogen assay for S07 *Bacillus subtili* cells using a monosaccharide array wherein half of the array has been treated with a maleimide PEG (mPEG-MAL) to cap the residual cyclopentadiene groups as depicted in FIG. 29.
Figure 34:
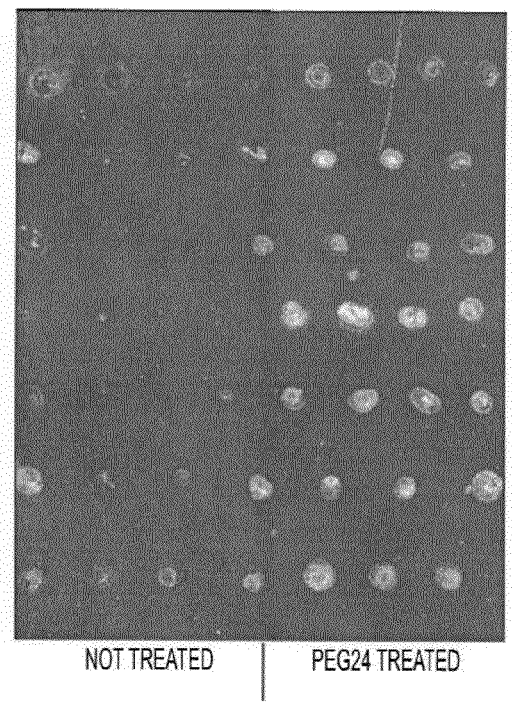
FIG. 34 is a scanned image of a pathogen assay for S05 *E. coli* cells using a monosaccharide array wherein half of the array has been treated with a maleimide PEG (mPEG-MAL) to cap the residual cyclopentadiene groups as depicted in FIG. 29.
Figures 35, 36:
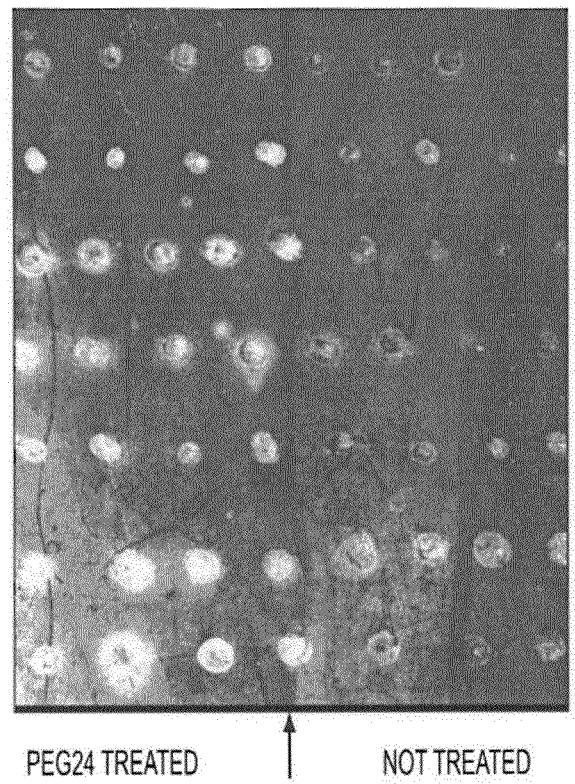
FIG. 35 is a scanned image of a pathogen assay for S06 *E. coli* cells using a monosaccharide array wherein half of the array has been treated with a maleimide PEG (mPEG-MAL) to cap the residual cyclopentadiene groups as depicted in FIG. 29.
FIG. 36 is a schematic depicting the spotting pattern for an assay using a sugar array on a polyacrylic hydrazide treated glass substrate.

Half of the slide was exposed to 50 μl of maleimido-PEG-24-Me (5 mg/ml in water) while the other half was covered with a cover glass lid as shown in FIG. 30. The spotted slide was incubated for 16 hours at room temperature.

Results and Observation

The PEG-treated surface is more hydrophilic than cyclopentadiene surface but less hydrophilic than the sugar spots.

Contact Angles:

Cyclopentadiene surface: 63
PEG-treated surface: 45
Sugar spot: Completely wettable.

Reference

Houseman et al., Carbohydrate Arrays For The Evaluation Of Protein Binding And Enzymatic Modification, Chem. Biol. 9, 443-454 (2002b).

Pathogen Cell Assay on mPEG-MAL Treated Monosaccharide Array

The reaction scheme for this assay is depicted in FIG. 38. The spotting pattern for the assay is shown in FIG. 39. The results for this assay are shown in FIGS. 40-43.

Materials

FITC-lectin *Triticum vulgaris* (wheat), Sigma L4895 (alpha and beta-GlcNAc specific)

FITC-lectin *Lens culinaris* (lentil), Sigma L9262 (alpha-man specific)

Vybrant dye Cycle Green stain 5 mM in DMSO (V35004, Invitrogen)

Pathogen cells: cultistik *Bacillus Subtili* (29446-606), kwik-stik *E. Coli* (2449-074), *Listeria Innocua* (29450-126), kwik-stik *Staph Epidermis* (29446-524)

Arrays were spotted on both cyclopentadiene vapor deposited (VD) slides and nitrocellulose slides (Fullmoon biosystems type C slides).

Procedure

Cell Cultures

The cells were suspended in Dulbecco's Phosphate Buffered Saline (DPBS) with 0.2% Tween 20 and innoculated on Agar petri dish and incubated at 37° C. overnight. *E. coli* on LB agar, all other on BBL TSA.

The cells were harvested and suspended in PBS. OD 600 was measured to quantitate cell concentrations.

*Bacillus Subtili:* 0.23;
*E. Coli:* 0.57;
*Listeria Innocula:* 0.17; and
*Staph Epidermis:* 0.33.

The cells were diluted to 0.01 OD (by calculation, $10^7$ cells/ml) in DPBS buffer (containing 1 mM $Ca^{2+}$ and $Mn^{2+}$)

Assay

Applied 50 µl of the cell suspension on the array slide, covered with cover slide, and incubated for 1 hour at RT.

The slides were washed five times with DPBS.

Cell Staining

Vybrant dye (2 µl) was added to 1 ml DPBS and apply 50 µl to each slides.

Incubated for 1 hour at RT.

Scanning

The slides were scanned on an Axon scanner with excitation wavelength at 532 nm, PMT 800, high resolution, and medium sensitivity.

Results and Observation

PEG treatment significantly reduce the background signal.

PEG seemed to improve *E. coli* binding.

Reference

Disney et al., Chemistry & Biology, Vol. 11, 1701-1707, December, 2004

Detection of Pathogens Using Sugar Slides

Reaction Negative Control

Reaction buffer: 1×PBS with $MnCl_2$ (1.0 mM), and $CaCl_2$ (1.0 mM) (already purchased as DPBS buffer)

Reaction Positive Control

Lectin in 1× reaction buffer

FITC-lectin *Triticum vulgaris* (wheat), Sigma L4895 (alpha and beta-GlcNAc specific) 20 µg/ml Non-pathogenic *E. coli* (density)—The cells were diluted to 0.01 OD (by calculation, $10^7$ cells/ml) in DPBS.

Pathogens to Test

*Bordetella, S. pyogenes,* and *E. coli* (pathogenic)

Influenza-A and adenovirus

Culturing of Bacteria

*E. coli* is cultured in LB broth and stored with 15% glycerol at −80° C.

cfu is determined by serial dilutions and cultured on LB plates

Procedure

Prepare all samples in final 50 µl of 1× reaction buffer

Prepare slides by placing down gaskets of 8 wells

Add samples into wells

Incubate at room temperature for 1 to 2 hour with shaking with cover to avoid evaporation.

Aspirate and remove the samples from slides

Wash with 50 µl of wash buffer (DPBS) at room temperature for 1 minute with shaking.

Repeat wash three times.

Add vibrant orange dye 50 µl and incubate at room temperature for 1.0 hour with shaking. The dye was prepared by adding 5 µl of stock into 1.0 ml of DPBS.

Wash with 50 µl of wash buffer (DPBS) at room temperature for 1 minute with shaking.

Repeat wash five times.

Scan the slides on an Axon scanner using excitation 532 nm.

While the foregoing specification teaches the principles of the present invention, with examples provided for the purpose of illustration, it will be appreciated by one skilled in the art from reading this disclosure that various changes in form and detail can be made without departing from the true scope of the invention.

---

What is claimed is:

1. An apparatus comprising:
a support having an upper surface comprising a plurality of discrete analyte binding areas arranged in a spaced relationship, wherein each of the discrete analyte binding areas comprises an immobilized macromolecule which comprises one or more ligand moieties which specifically bind to a target analyte and;
a cover spaced from the upper surface of the support and forming a flow channel therebetween, the cover having a first surface facing toward the support and a second surface facing away from the support;
wherein at least one discrete area comprises an immobilized macromolecule which comprises a plurality of carbohydrate ligands, wherein the carbohydrate ligands comprise a plurality of lectin moieties, wherein the immobilized macromolecule which comprises a plurality of lectin moieties comprises one or more pendent groups of the formula:

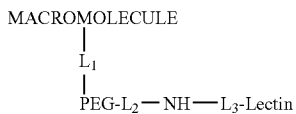

wherein "MACROMOLECULE" represents the immobilized macromolecule, "PEG" is a telechelic poly(ethylene oxide) moiety, "Lectin" is a lectin moiety and $L_1$, $L_2$ and $L_3$ are each, independently, a covalent bond or a linking group.

2. The apparatus of claim 1 wherein at least one discrete area comprises an immobilized macromolecule which has a molecular weight of at least 100 Da.

3. The apparatus of claim 1, wherein at least one discrete area comprises an immobilized macromolecule which has a molecular weight of: 100 to 5,000,000 Da; 1,000 to 2,000,000 Da; or 10,000 to 1,000,000 Da.

4. The apparatus of claim 1, wherein at least one discrete area comprises an immobilized macromolecule which comprises at least 1 ligand per molecule.

5. The apparatus of claim 4, wherein the immobilized macromolecule comprises a plurality of ligand moieties per molecule.

6. The apparatus of claim 1, wherein at least one discrete area comprises an immobilized macromolecule which comprises: from 1 to 500,000 ligand moieties per molecule; from 5 to 50,000 ligand moieties per molecule; or from 100 to 1,000 ligand moieties per molecule.

7. The apparatus of claim 1, wherein at least one discrete area comprises at least one immobilized macromolecule which comprises at least two different ligand moieties.

8. The apparatus of claim 1, wherein at least one discrete area comprises a plurality of different immobilized macromolecules.

9. The apparatus of claim 1, wherein the first surface of the cover comprises polyethylene glycol moieties.

10. The apparatus of claim 1, wherein regions of the upper surface of the support adjacent and/or between the discrete analyte binding areas comprise mPEG moieties.

11. The apparatus of claim 1, wherein the cover is optically transparent.

12. The apparatus of claim 1, wherein the support comprises a material selected from the group consisting of mica, silica, glass, quartz, indium-tin oxide (ITO), alumina, and a polymer.

13. The apparatus of claim 12, wherein the support comprises a polymer selected from the group consisting of poly(dimethyl siloxane) (PDMS), poly(meth)acrylates, poly(methyl methacrylate) (PMMA), polyesters, poly(ethylene terephthalate) (PET), polyamides, poly(meth)acrylamides, polycarbonates, polystyrene (PS), polyalkenes, polyalkynes, poly(cyclic olefin)s, their copolymers, or blends thereof.

14. The apparatus of claim 1, wherein the one or more ligand moieties specifically bind to a target pathogenic cell.

* * * * *